United States Patent
Elmaleh

(10) Patent No.: US 9,918,992 B2
(45) Date of Patent: Mar. 20, 2018

(54) COMBINATION THERAPIES FOR THE TREATMENT OF ALZHEIMER'S DISEASE AND RELATED DISORDERS

(71) Applicant: The General Hospital Corporation, Boston, MA (US)

(72) Inventor: David R. Elmaleh, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/046,489

(22) Filed: Feb. 18, 2016

(65) Prior Publication Data

US 2016/0158192 A1    Jun. 9, 2016

Related U.S. Application Data

(62) Division of application No. 14/437,316, filed as application No. PCT/US2013/066069 on Oct. 22, 2013, now Pat. No. 9,855,276.

(60) Provisional application No. 61/718,303, filed on Oct. 25, 2012.

(51) Int. Cl.
| | |
|---|---|
| A61K 31/428 | (2006.01) |
| A61K 45/06 | (2006.01) |
| A61K 31/5415 | (2006.01) |
| A61K 31/192 | (2006.01) |
| A61K 31/352 | (2006.01) |
| A61K 31/438 | (2006.01) |
| A61K 31/706 | (2006.01) |
| A61K 31/047 | (2006.01) |
| A61K 31/225 | (2006.01) |
| A61K 31/435 | (2006.01) |
| A61K 51/04 | (2006.01) |
| A61K 31/13 | (2006.01) |
| A61K 31/194 | (2006.01) |
| A61K 31/075 | (2006.01) |
| A61K 31/55 | (2006.01) |
| A61K 31/713 | (2006.01) |
| A61K 38/18 | (2006.01) |
| A61K 39/00 | (2006.01) |
| C07K 16/18 | (2006.01) |
| A61K 31/353 | (2006.01) |
| A61K 48/00 | (2006.01) |

(52) U.S. Cl.
CPC ........ *A61K 31/5415* (2013.01); *A61K 31/047* (2013.01); *A61K 31/075* (2013.01); *A61K 31/13* (2013.01); *A61K 31/192* (2013.01); *A61K 31/194* (2013.01); *A61K 31/225* (2013.01); *A61K 31/352* (2013.01); *A61K 31/353* (2013.01); *A61K 31/428* (2013.01); *A61K 31/435* (2013.01); *A61K 31/438* (2013.01); *A61K 31/55* (2013.01); *A61K 31/706* (2013.01); *A61K 31/713* (2013.01); *A61K 38/185* (2013.01); *A61K 39/0005* (2013.01); *A61K 45/06* (2013.01); *A61K 51/0453* (2013.01); *C07K 16/18* (2013.01); *A61K 48/00* (2013.01)

(58) Field of Classification Search
CPC ...... A61K 31/352; A61K 45/06; A61K 31/48; A61K 31/192; A61K 31/194
See application file for complete search history.

(56) References Cited

U.S. PATENT DOCUMENTS

| | | | |
|---|---|---|---|
| 3,419,578 A | 12/1968 | Fitzmaurice | |
| 3,686,412 A | 8/1972 | Fitzmaurice et al. | |
| 3,957,965 A | 5/1976 | Hartley et al. | |
| 4,120,285 A | 10/1978 | Nugent | |
| 4,429,545 A | 2/1984 | Steinberg | |
| 4,996,296 A | 2/1991 | Pecht et al. | |
| 5,567,720 A | 10/1996 | Averback | |
| 5,830,920 A | 11/1998 | Chucholowski et al. | |
| 6,197,963 B1 | 3/2001 | Hirschmann et al. | |
| 6,696,039 B2 | 2/2004 | Kung et al. | |
| 6,911,466 B2 * | 6/2005 | Koo | A61K 31/165 514/420 |
| 7,160,559 B1 | 1/2007 | McGee et al. | |
| 7,858,803 B2 | 12/2010 | Elmaleh et al. | |
| 8,381,454 B1 | 2/2013 | Robinson | |
| 8,613,920 B2 * | 12/2013 | Lieberburg | C07K 16/18 424/133.1 |
| 8,617,517 B2 | 12/2013 | Elmaleh et al. | |
| 8,765,742 B2 | 7/2014 | Hilfiker et al. | |

(Continued)

FOREIGN PATENT DOCUMENTS

| | | |
|---|---|---|
| CA | 2408793 A1 | 12/2001 |
| EP | 1632242 A2 | 3/2006 |

(Continued)

OTHER PUBLICATIONS

Schnabel News 2008; Earl results of Alzheimer's Passive Trial mixed).*
Deiana et al. Poster presentation (P2-428).*
Upashyaa et al. (African Journal of Pharmacy and Pharmacology vol. 4(6), pp. 408-421, Jun. 2010).*
Imbimbo ((Expert Opin. Investig. Drugs (2009) 18(8)1147-1168).*
Deiana, S. et al., "Methylthioninium Chloride Versus Rivastigmine and Their Co-Administration Efficacy in Reversing Scopolamine-Induced Cognitive Deficits in a Pharmacological Mouse Model of Alzheimer's Disease," Poster Presentation (P2-428) (2009).

(Continued)

*Primary Examiner* — Shirley V Gembeh
(74) *Attorney, Agent, or Firm* — Foley Hoag LLP

(57) ABSTRACT

The present invention relates to combination therapies for treating Alzheimer's disease or an amyloidosis-associated pathological condition comprising co-administering a therapeutically effective amount of a first compound, and a therapeutically effective amount of a second compound. In certain embodiments, the first compound or the second compound inhibits AB peptide polymerization; is an anti-inflammatory; improves cognitive function, mood, or social behavior; is associated with Tau or alpha-synuclein; or regulates amyloid peptide washout.

6 Claims, 14 Drawing Sheets

(56) References Cited

U.S. PATENT DOCUMENTS

| | | | |
|---|---|---|---|
| 9,283,230 | B2 | 3/2016 | Clunas et al. |
| 2002/0009491 | A1 | 1/2002 | Rothbard et al. |
| 2002/0016359 | A1 | 2/2002 | Hellberg et al. |
| 2002/0091100 | A1 | 7/2002 | Lezdey et al. |
| 2002/0107173 | A1 | 8/2002 | Friedhoff et al. |
| 2004/0176469 | A1* | 9/2004 | Thomas ............... A61K 31/00 514/649 |
| 2004/0259952 | A1 | 12/2004 | Abbas et al. |
| 2006/0240007 | A1* | 10/2006 | Sanders ............... A61K 31/445 424/144.1 |
| 2007/0015813 | A1 | 1/2007 | Carter et al. |
| 2007/0086981 | A1 | 4/2007 | Meijer et al. |
| 2007/0093457 | A1 | 4/2007 | Arber et al. |
| 2007/0107173 | A1 | 5/2007 | Yamada |
| 2007/0249644 | A1 | 10/2007 | Pearson et al. |
| 2009/0155256 | A1 | 6/2009 | Black et al. |
| 2010/0113613 | A1 | 5/2010 | McLaurin et al. |
| 2010/0143251 | A1 | 6/2010 | Tamagnan et al. |
| 2010/0173960 | A1* | 7/2010 | Cruz .................... A61K 31/047 514/375 |
| 2010/0234295 | A1 | 9/2010 | Chen |
| 2010/0298389 | A1 | 11/2010 | Elmaleh et al. |
| 2011/0132434 | A1 | 6/2011 | Correia et al. |
| 2011/0262442 | A1 | 10/2011 | Hamilton et al. |
| 2012/0058049 | A1 | 3/2012 | Elmaleh et al. |
| 2012/0121656 | A1 | 5/2012 | Watson et al. |
| 2012/0175082 | A1 | 7/2012 | Kmetovicz et al. |
| 2014/0140927 | A1 | 5/2014 | Elmaleh et al. |
| 2014/0228304 | A1 | 8/2014 | Jones et al. |

FOREIGN PATENT DOCUMENTS

| | | | |
|---|---|---|---|
| EP | 2322163 | A1 | 5/2011 |
| EP | 2377860 | A1 | 10/2011 |
| GB | 1144906 | A | 3/1969 |
| GB | 1257162 | A | 12/1971 |
| WO | WO-90 09789 | A2 | 9/1990 |
| WO | WO-02/28820 | A1 | 4/2002 |
| WO | WO-03/045331 | A2 | 6/2003 |
| WO | WO-2007/094718 | A1 | 8/2007 |
| WO | WO-2008/013799 | A2 | 1/2008 |
| WO | WO 2008131298 | * | 10/2008 |
| WO | WO-2009/133128 | A1 | 11/2009 |
| WO | WO-2010/088455 | A2 | 8/2010 |
| WO | WO-2015/002703 | A1 | 1/2015 |
| WO | WO-2015/061397 | | 4/2015 |

OTHER PUBLICATIONS

Gasparini, L. et al., "Non-steroidal anti-inflammatory drugs (NSAIDs) in Alzheimer's disease: old and new mechanisms of action," Journal of Neurochemistry, 2004, 91, 521-536.

Guchardi, R. et al., "Influence of fine lactose and magnesium stearate on low dose dry powder inhaler formulations," International Journal of Pharmaceutics 348 (2008) 10-17.

Cairns, et al., Synthesis and Structure-Activity Relationships of Disodium Cromoglycate and Some Related Compounds, Journal of Medicinal Chemistry, 1972, 15(6):583-589.

Pratico D: "Alzheimer's disease and non-steroidal antiinflammatory drugs: Old therapeutic tools with novel mechanisms of action?", Current Medicinal Chemistry—Central Nervous System Agents, vol. 5, No. 2, pp. 111-117, 2005.

Reverchon et al., "Production of Cromolyn Sodium Microparticles for Aerosol Delivery by Supercritical Assisted Atomization," AAPS PharmSciTech 2007; 8(4) Article 114, Dec. 21, 2007.

STN database CAS RN: 16110-51-3 (Nov. 16, 1984).

Gilani et al., "Influence of Formulation Variables and Inhalation Device on the Deposition Profiles of Cromolyn Sodium Dry Powder Aerosols," Daru vol. 12, No. 3, p. 123-130, 2004.

Lim et al., "Ibuprofen Suppresses Plaque Pathology and Inflammation in a Mouse Model of Alzheimer's Disease," The Journal of Neuroscience, Aug. 1, 2000, 20(15):5709-5714.

PCT International Search Report and Written Opinion, PCT/US2010/022495, Nov. 11, 2010, 11 pages.

European Extended European Search Report, EP 10736439, Jun. 19, 2012, 9 pages.

International Search Report and Written Opinion dated Mar. 13, 2014 in connection with PCT/ US2013/066069.

Imbimbo, "An update on the efficacy of non-steroidal anti-inflammatory drugs in Alzheimer's disease," Expert Opinion on Investigational Drugs, 2009; 18(8), pp. 1147-1168.

Lanz et al., "The γ-Secretase Inhibitor N-[N-(3,5-Difluorophenacetyl)-L-alanyl]-S-phenylglycine t-butyl Ester Reduces Aβ Levels in Vivo in Plasma and Cerebrospinal Fluid in Young (Plaque-Free) and Aged (Plaque-Bearing) Tg2576 Mice" The Journal of Pharmacology and Experimental Therapeutics, vol. 305, No. 3, 2003, pp. 864-871.

Sun et al., "Synthesis of scyllo—inositol derivatives and their effects on amyloid beta peptide aggregation," Bioorganic & Medicinal Chemistry 16 (2008), pp. 7177-7184.

Bulic et al., "Tau protein and tau aggregation inhibitors," Neuropharmacology, 59: 276-289 (2010).

Cacabelos, R., "Donepezil in Alzheimer's disease: From conventional trials to pharmacogenetics," Neuropsychiatric Disease and Treatment 2007:3(3), pp. 303-333.

Chen et al., "Current experimental therapy for Alzheimer's Disease," Curr Neuropharmacol, 5(2): 127-134 (2007).

Extended European Search Report issued by the European Patent Office in corresponding International Application No. 14855211.0, dated May 29, 2017.

Galimberti et al., "Disease-modifying treatments for Alzheimer's disease," Ther Adv Neurol Disord, 4(4): 203-216 (2011).

International Search Report and Written Opinion for International Application No. PCT/US2010/022495 dated Nov. 10, 2010.

International Search Report and Written Opinion for International Application No. PCT/US2014/061694 dated Jan. 2, 2015.

Loeb et al., "A randomized, controlled trial of doxycycline and rifampin for patients with Alzheimer's disease," J AM Geriatr Soc, 52(3): 381-7 (2004).

Mandel, "CERE-110, an adeno-associated virus-based gene delivery vector expressing human nerve growth factor for the treatment of Alzheimer's disease," Curr Opin Mol Ther, 12(2): 240-247 (2010).

Morihara et al., "Ibuprofen Suppresses Interleukin-I13 Induction of Pro-Amyloidogenic alpha1-Antichymotrypsin to Ameliorate beta-Amyloid A-beta Pathology in Alzheimer's Models," Neuropsychopharmacology (2005) 30, 1111-1120.

Sabbagh et al., "Latrepirdine, a potential novel treatment for Alzheimer's disease and Huntington's chorea," Curr Opin Investig Drugs, 11(1): 80-91 (2010).

Wang et al. "Allopregnanolone reverses neurogenic and cognitive deficits in mouse model of Alzheimer's disease," PNAS, 107(14): 6498-6503 (2010).

\* cited by examiner

COMBINATION THERAPIES FOR THE TREATMENT OF ALZHEIMER'S DISEASE AND RELATED DISORDERS

CROSS-REFERENCE TO RELATED APPLICATIONS

This is a divisional application of U.S. patent application Ser. No. 14/437,316, filed Apr. 21, 2015, which represents the national stage entry of PCT International Application PCT/US2013/066069 filed Oct. 22, 2013, which claims the benefit of U.S. Provisional Patent Application 61/718,303, filed Oct. 25, 2012, which are incorporated herein by reference for all purposes.

BACKGROUND

Alzheimer's disease (AD) is a progressive neurodegenerative disorder of the brain, which is characterized by the memory deterioration, behavioral disturbances, impairment of activities of daily living, and loss of independent function. It is thought that 18-24 million people in the world are currently suffering from AD, two-thirds of whom are living in developed or developing countries. This number is expected to reach 34 million by 2025.

AD is a complicated disease. It may even be the result of more than one disease. It is characterized by an accumulation otinsoluble aggregates of amyloid-beta peptide (Aβ). such as Aβ oligomers. These aggregates or oligomers are associated with cell inflammatory response and are thought to bind to a surface receptor on neurons and change the structure of the synapse, thereby disrupting neuronal communication. Due to the minute amount produced per day (22-27 ng/day) and accumulated for years (about 7-10 mg in brains of AD subjects), this daily inflammatory response is invisible and not associated with any major symptoms. In addition, tau protein abnormalities are thought to play a role in the disease cascade. Hyperphosphorylated tau proteins are thought to pair with other threads of tau. Eventually, they form neurofibrillary tangles inside nerve cell bodies. When this occurs, the microtubules disintegrate, collapsing the neuron's transport system. This may result first in malfunctions in biochemical communication between neurons and later in the death of the cells.

The recent failures of several promising drugs have spurred greater urgency to investigate new targets and their interconnectedness. That said, new therapies for Alzheimer's are needed.

SUMMARY OF THE INVENTION

In certain embodiments, the invention relates to a method of treating a disease or condition in a subject in need thereof comprising co-administering a therapeutically effective amount of a first compound, and a therapeutically effective amount of a second compound, wherein the disease or condition is Alzheimer's disease, dementia, an amyloidosis-associated condition, or a head injury.

In certain embodiments, the invention relates to a method of slowing the progression of a disease or condition in a subject in need thereof comprising co-administering a therapeutically effective amount of a first compound, and a therapeutically effective amount of a second compound, wherein the disease or condition is Alzheimer's disease, dementia, an amyloidosis-associated condition, or a head injury.

In certain embodiments, the invention relates to any one of the aforementioned methods, wherein the first compound inhibits Aβ peptide polymerization; and the second compound is an anti-inflammatory.

In certain embodiments, the invention relates to any one of the aforementioned methods, wherein the first compound is an anti-inflammatory; and the second compound improves cognitive function, mood, or social behavior.

In certain embodiments, the invention relates to any one of the aforementioned methods, wherein the first compound inhibits Aβ peptide polymerization; and the second compound improves cognitive function, mood, or social behavior.

In certain embodiments, the invention relates to any one of the aforementioned methods, wherein the first compound is an anti-inflammatory; and the second compound is associated with Tau or alpha-Synuclein.

In certain embodiments, the invention relates to any one of the aforementioned methods, wherein the first compound is an anti-inflammatory; and the second compound modulates amyloid peptide formation and washout.

In certain embodiments, the invention relates to any one of the aforementioned methods, wherein the first compound and the second compound inhibit Aβ peptide polymerization.

In certain embodiments, the invention relates to any one of the aforementioned methods, wherein the first compound and the second compound are anti-inflammatories.

In certain embodiments, the invention relates to any one of the aforementioned methods, wherein the first compound and the second compound improve cognitive function, mood, or social behavior.

In certain embodiments, the invention relates to any one of the aforementioned methods, wherein the first compound and the second compound are associated with Tau or alpha-Synuclein.

In certain embodiments, the invention relates to any one of the aforementioned methods, wherein the first compound and the second compound modulate amyloid peptide formation and washout.

In certain embodiments, the compound inhibiting AP peptide polymerization is selected from the group consisting of formula I-IV:

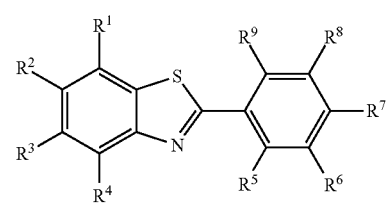

I

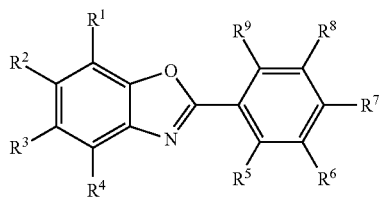

II

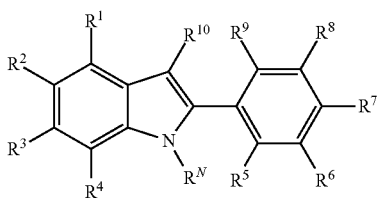

III

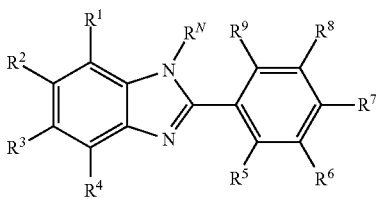

IV

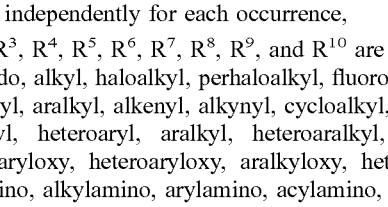

wherein, independently for each occurrence, $R^1$, $R^2$, $R^3$, $R^4$, $R^5$, $R^6$, $R^7$, $R^8$, $R^9$, and $R^{10}$ are hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —Y-(haloalkylene)-alkyl;

$R^7$ is hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamine, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamide, formyl, cyano, isocyano, —Y-(haloalkylene)-alkyl, or —Y-(haloalkylene)-R;

$R^N$ is hydrogen, lower alkyl, or -(haloalkylene)-alkyl;

Y is a bond, $N(R^N)$, O, or S; and

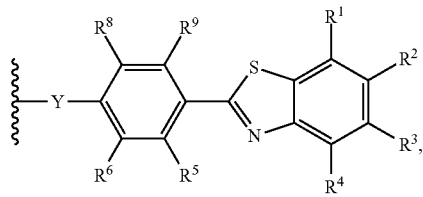

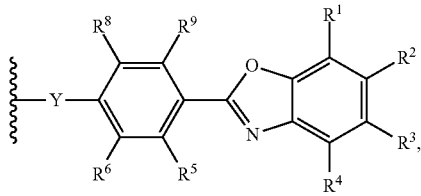

R is

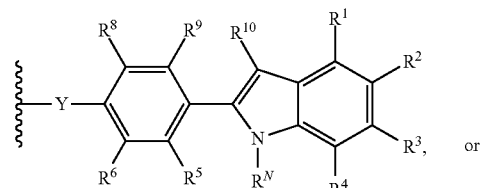

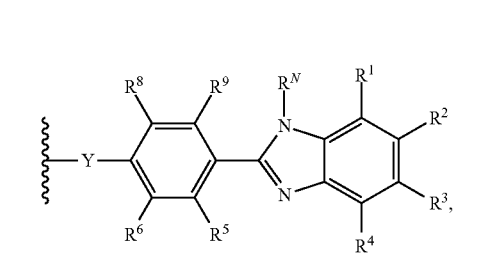

provided that at least one of $R^1$, $R^2$, $R^3$, $R^4$, $R^5$, $R^6$, $R^7$, $R^8$, $R^9$, or $R^{10}$ is —Y-(haloalkylene)-alkyl; or $R^N$ is -(haloalkylene)-alkyl.

In certain embodiments, the Aβ peptide polymerization inhibitor is

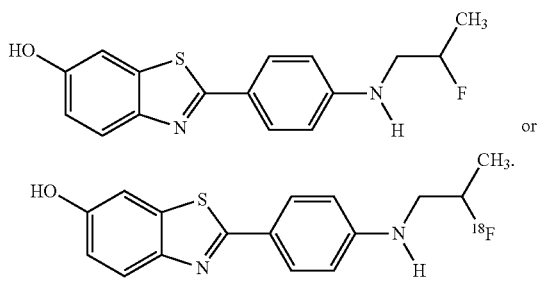

In certain embodiments, the Aβ peptide polymerization inhibitor is

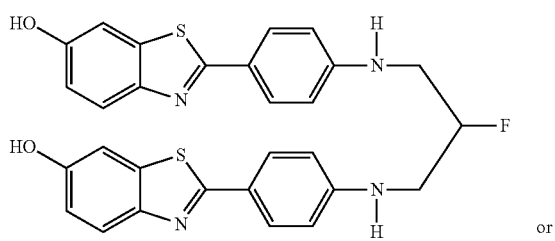

-continued

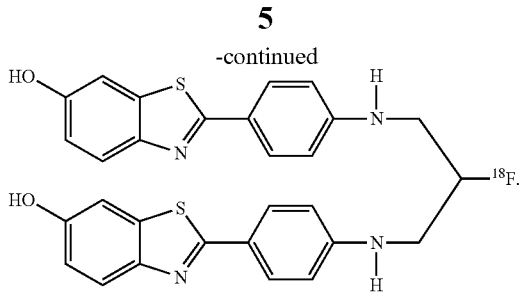

BRIEF DESCRIPTION OF THE DRAWINGS

In FIG. 7, a 5, 30 or 60 minute, corresponding to Series 1, 2 or 3, respectively in the graph, brain uptake shows 1% accumulation with little or no washout for the period measured.

DESCRIPTION OF THE INVENTION

Therapeutic Agents

Figure 1:
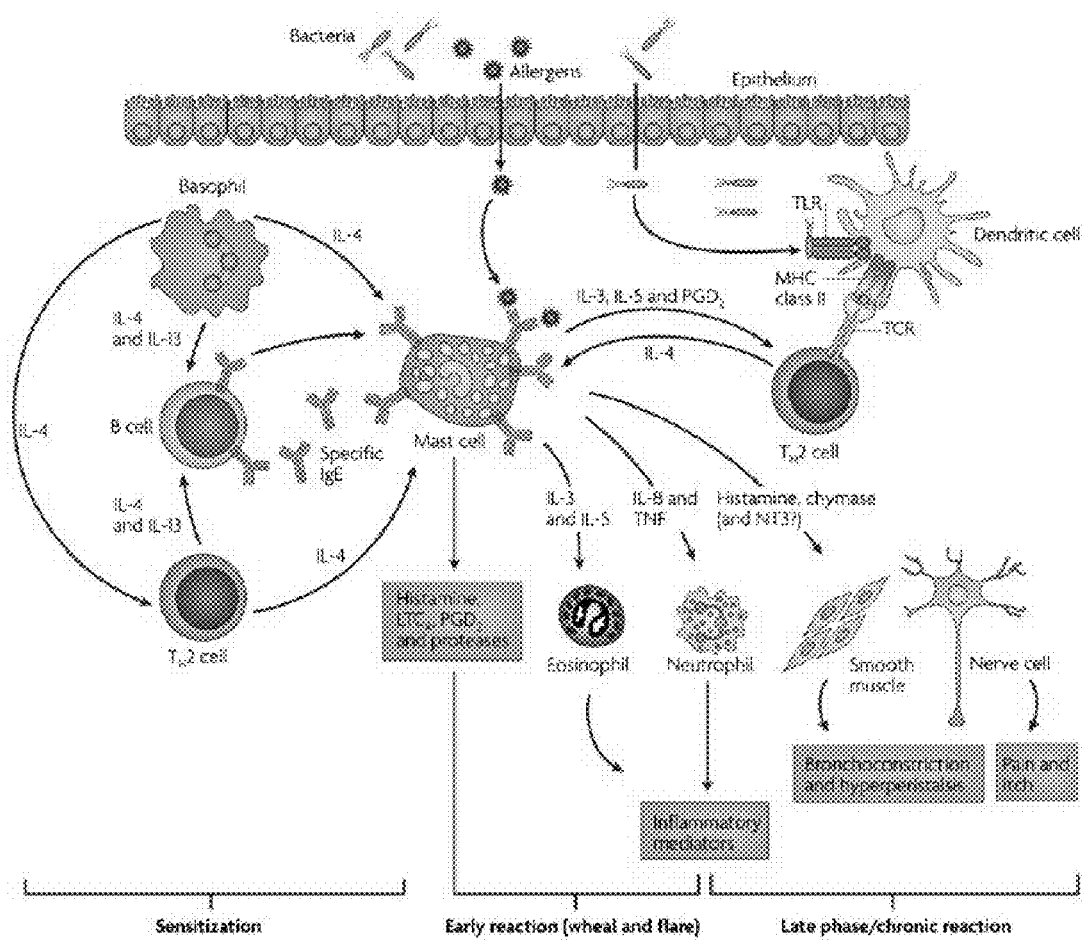
FIG. 1 depicts various functions of mast cell agents.
Figure 2:
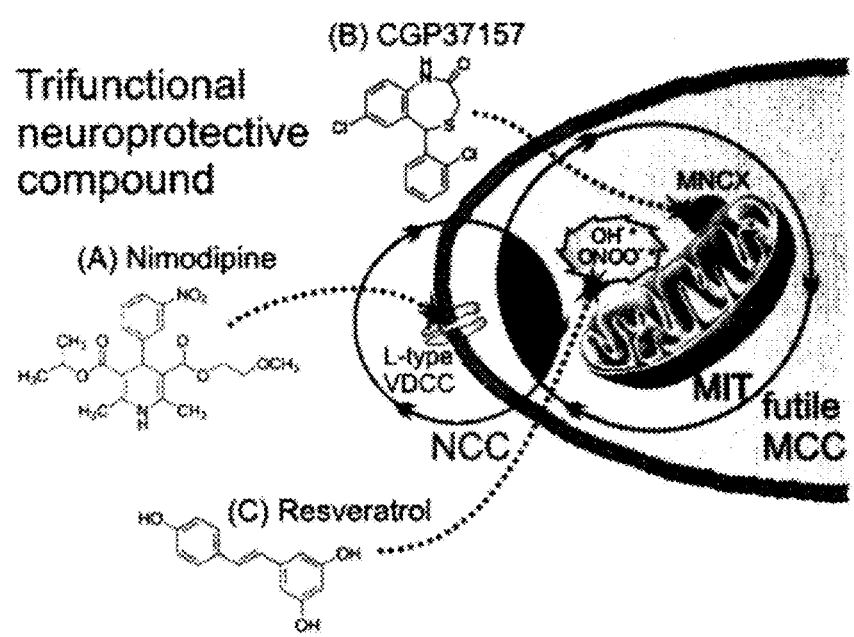
FIG. 2 depicts a three-drug combination.
Figure 3:
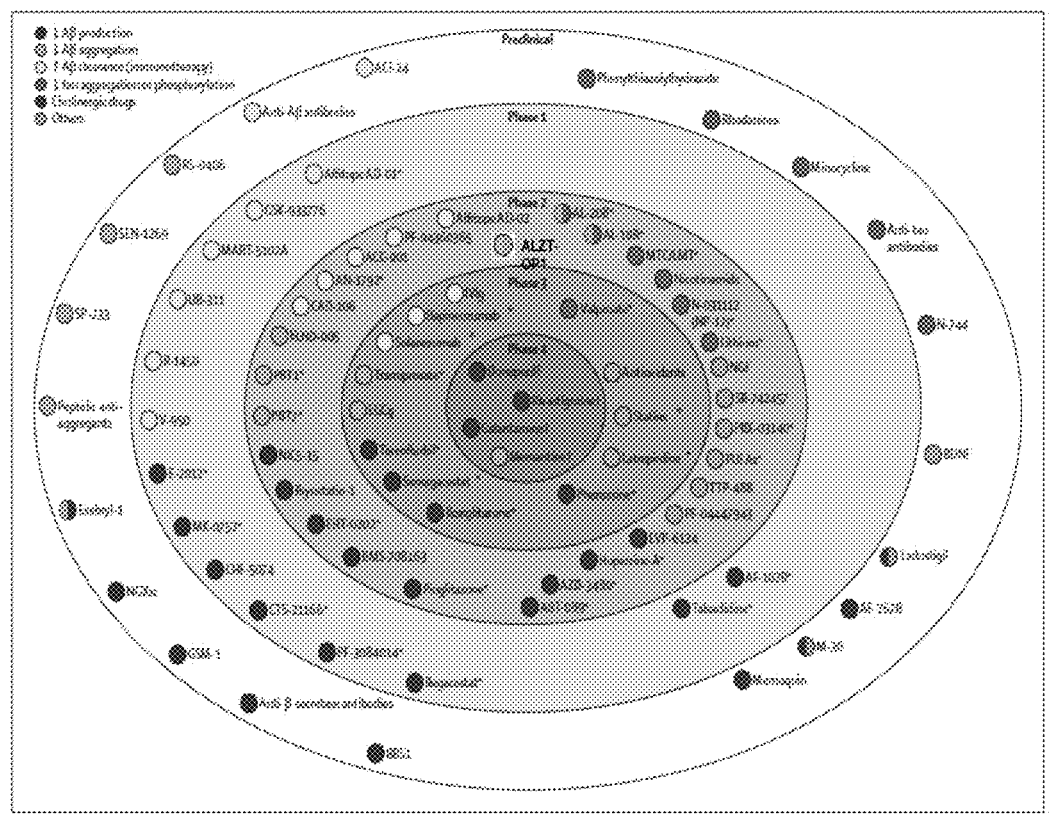
FIG. 3 depicts various therapeutic agents of the invention and their respective proposed mechanisms of action in monotherapy.

Featured herein are methods of treating or preventing an amyloidosis-associated condition in a subject in need thereof comprising administering to the subject a therapeutically effective amount of at least two compounds selected from the group consisting of an Aβ peptide polymerization inhibitor, an anti-inflammatory; a compound that improves cognitive function, mood, or social behavior, a compound associated with Tau or alpha-Synuclein and a compound that regulates amyloid peptide washout. The methods involve multifunctional treatment combinations and dosing.

These combination treatments may slow down memory loss or brain degeneration in early stages of AD. For example, a subject may be exhibiting mild cognitive impairment (MCI), or may have a narrow MMSE (mini-mental state examination) score of between about 24 and about 28.

These combination treatments may also be administered to subjects with AD. In certain embodiments, the subjects experience improved quality of life.

Aβ-Peptide Polymerization Inhibitors

Thioflavin or [N-methyl-($^{11}$C)]2-(4'-methylaminophenyl)-6-hydroxybenzothiazole(PIB) is an Aβ peptide polymerization inhibitor.

Aβ peptide polymerization inhibitors are also represented by formula I-IV:

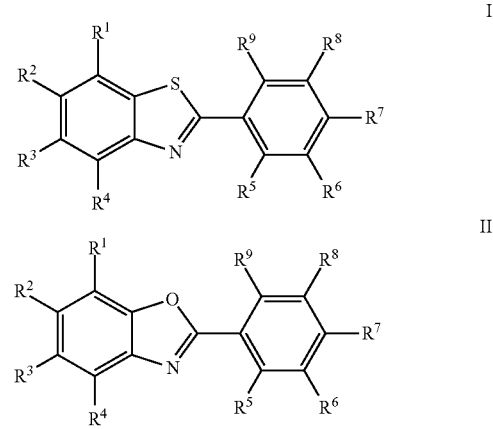

-continued

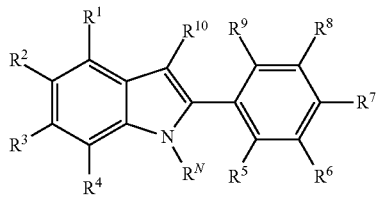
III

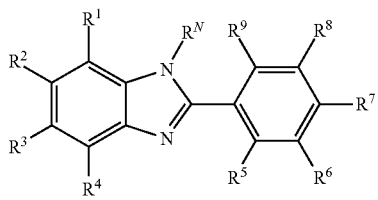
IV wherein, independently for each occurrence,
$R^1$, $R^2$, $R^3$, $R^4$, $R^5$, $R^6$, $R^7$, $R^8$, $R^9$, and $R^{10}$ are hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —Y-(haloalkylene)-alkyl;

$R^7$ is hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamine, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamide, formyl, cyano, isocyano, —Y-(haloalkylene)-alkyl, or —Y-(haloalkylene)-R;

$R^N$ is hydrogen, lower alkyl, or -(haloalkylene)-alkyl;
Y is a bond, $N(R^N)$, O, or S; and R is

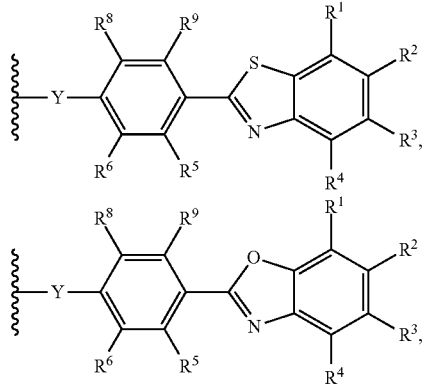

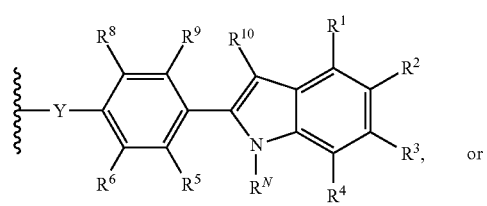
or

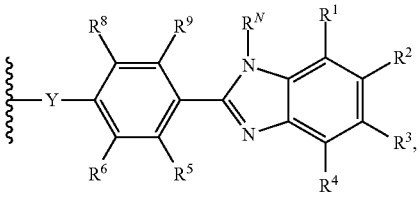

provided that at least one of $R^1$, $R^2$, $R^3$, $R^4$, $R^5$, $R^6$, $R^7$, $R^8$, $R^9$, or $R^{10}$ is —Y-(haloalkylene)-alkyl; or $R^N$ is -(haloalkylene)-alkyl.

In certain embodiments, the Aβ peptide polymerization inhibitor is

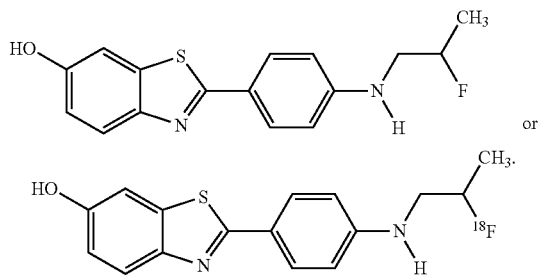

In certain embodiments, the Aβ peptide polymerization inhibitor is

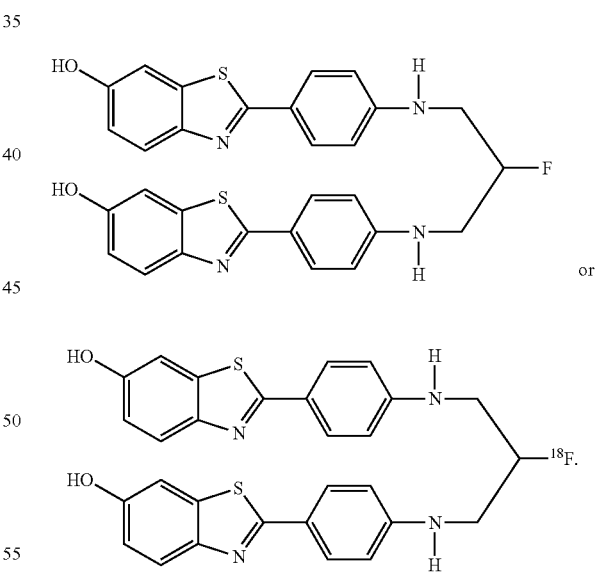

The following U.S. patents and patent applications, which are hereby incorporated by reference in their entirety, also describe Aβ peptide polymerization inhibitors: U.S. Pat. No. 7,858,803; U.S. Pat. Nos. 6,972,127; 6,946,116; 6,696,039; U.S. Pat. Nos. 6,168,776; 5,594,142; 4,481,206; 4,405,735; and U.S. Patent Application Publication No. 2011/0060138.

Additional Aβ peptide polymerization inhibitors may be selected from the group consisting of:

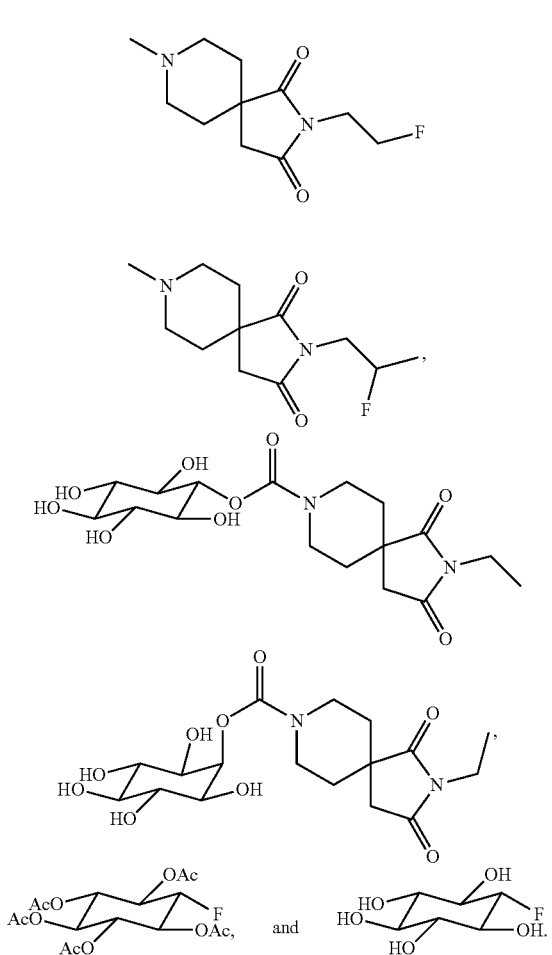

A gamma secretase inhibitor, such as LY451039 (Semagacestat, Eli Lily) may also function as an Aβ peptide polymerization inhibitor. Metal ionophores, such as PBT2 (Prana), which target metal-induced aggregation of Aβ may also function as an Aβ peptide polymerization inhibitor. Statins may also function as Aβ peptide polymerization inhibitors.

Endocannabinoids, such as arachidonoylethanolamine, tetrahydrocannabinol, 2-arachidonoyl glycerol, 2-arachidonyl glyceryl ether, N-arachidonoyl-dopamine, or virodhamine are further examples of Aβ peptide polymerization inhibitors.

An appropriate Aβ peptide polymerization inhibitor should slow the rate of Aβ peptide polymerization by at least about three times slower, about five times slower, about seven times slower, about 10 times slower, about 15 times slower, about 20 times slower, about 25 times slower, about 30 times slower, about 35 times slower, about 40 times slower, about 45 times slower, about 50 times or about 100 times slower than the rate of Aβ peptide polymerization in the absence of the inhibitor.

An appropriate Aβ peptide polymerization inhibitor should have appropriate structures (size, lipophilicity, and charge) to allow for penetration of the blood brain barrier (BBB). In addition the Aβ peptide polymerization inhibitor may have specific affinity for solubilizing and interacting with oligomers to prevent them from aggregating.

The daily required dose administration should be proportional to the approximate daily quantity of Aβ peptide; this dosing regimen minimizes side effects from extensive dosing. Appropriate log P, polar surface area (PSA) and % PSA should determine brain permeability and drug effectiveness.

An estimation of the amount of deposited amyloid-β in the brain requires data that have a sufficient sample size and are derived from quantitative assay systems that are combined with aggressive, formic acid extraction protocols. Assuming that the average weight of an AD brain is 1,150 g and the grey matter of the cortex, which contains the majority of deposited amyloid-β, comprises 42% of the weight of the brain, Gravina et al. calculated that ~10 mg of amyloid-β per brain is deposited, whereas Naslund et al. calculated that ~4 mg of amyloid-β per brain is deposited. Although the result obtained by Naslund et al. is lower than other literature estimates, for the purposes of this analysis the total amount of Aβ in a human AD brain at end-stage disease is assumed to be derived from 10 mg of Aβ-plaque.

It is important to compare the amount of amyloid-β that is deposited in the AD brain with the overall rate of amyloid-β production, to provide a conceptual framework for this aspect of the disease process and to place into context the potential for different amyloid-β-centric therapeutics to mediate a therapeutic effect. Therefore the estimated amount produced per day is less than 25 ng per day.

In certain embodiments, the Aβ peptide polymerization inhibitor is administered in nM concentrations.

Anti-Inflammatory Compounds

Anti-inflammatory compounds may be mast cell stabilizers, such as cromolyn, a cromolyn derivative, a cromolyn analog, such as those described in U.S. Patent Application Publication No. 2012/0058049, which is hereby incorporated by reference in its entirety, eugenol, nedocromil, pemirolast, olopataidne, alfatoxin $G_1$ alfatoxin B1, alfatoxin $M_1$ deoxynivalenol, zearalenone, ochratoxin A, fumonisin $B_1$ hydrolyzed fumonisin $B_1$ patulin, ergotamine,

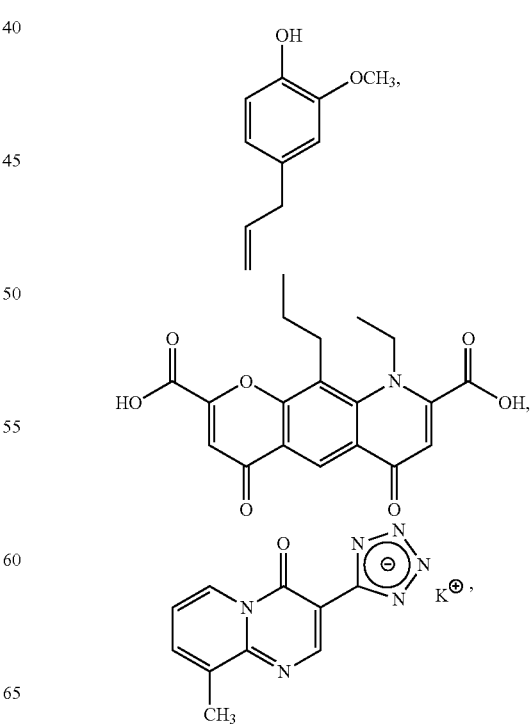

-continued

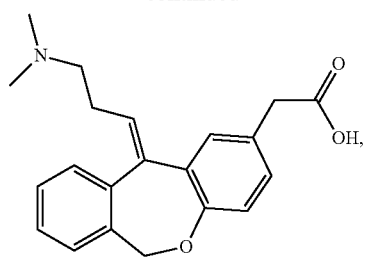

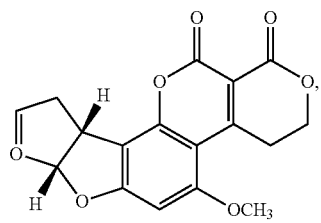

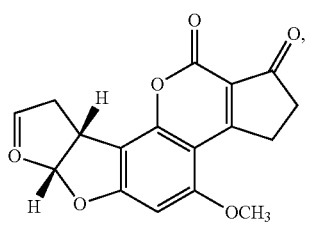

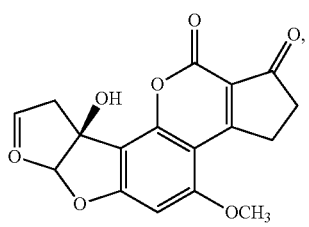

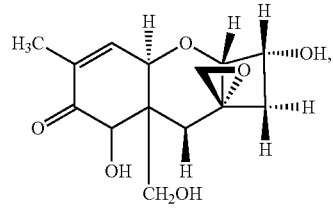

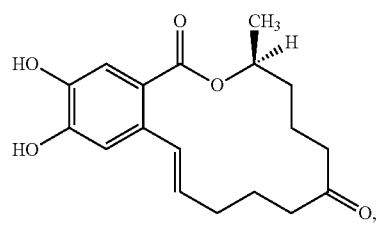

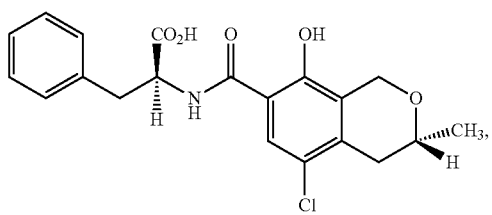

-continued

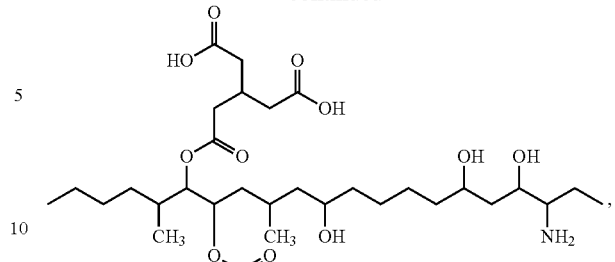

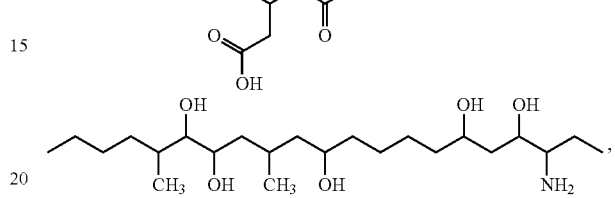

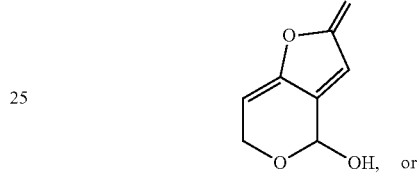, or

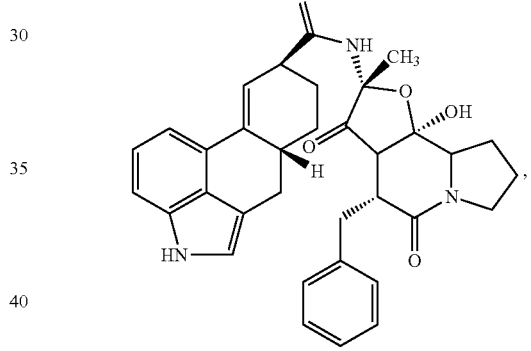

Anti-inflammatory compounds may also be a non-steroidal anti-inflammatory drug (NSAID), such as acetylsalicylic acid, diflunisal, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, licofelone, hyperforin, or figwort.

Since the inflammatory response to Aβ peptide production has invisible side effect symptoms, dosing control is important for preventing systemic side effect toxicity and worsening outcome.

Compounds that Improve Cognitive Function, Mood and/or Social Behavior

Agents for improving cognitive function, mood, and/or social behavior include cholinesterase inhibitors, such as donepezil, riastigmine, or galantamine. Other examples include N-methyl-D-aspartate (NMDA) receptor antagonists, such as memantine. Antioxidants, such as vitamin E or selegiline may also improve a subject's cognitive function, mood and/or social behavior. Allopregnanolone, a neurosteroid present in the blood is another example of an agent that improves cognitive function, mood, or social behavior in a subject.

Agents that initiate and/or amplify a subject's immune response, such as a tumor necrosis factor (TNF) inhibitor, e.g. etanercept or antibiotics, such as doxycycline, rifampin, or minocycline, are also agents that improve cognitive function, mood, or social behavior.

Spiro-(N'-methyl-piperidyl-4')-N-ethyl-succinimide, as described in U.S. Pat. No. 4,481,206, which is hereby incorporated by reference in its entirety, is another example of an agent that improves cognitive function, mood or social behavior. This molecule improves cognitive function by compensatory activation of other receptors for improving nerve communication and cognition. These agents are traditionally used to improve the quality of life of subjects with onset and disease progression.

Latrepirdine appears to operate through multiple mechanisms of action, both blocking the action of neurotoxic beta-amyloid proteins and inhibiting L-type calcium channels, modulating the action of AMPA and NMDA glutamate receptors, and may exert a neuroprotective effect by blocking a novel target that involves mitochondrial pores, which are believed to play a role in the cell death that is associated with neurodegenerative diseases and the aging process.

R3487 (Roche) is a partial agonist of the nicotinic alpha-7 receptor, a highly specialized receptor found in the central nervous system. In a recently completed Phase 2a study in Alzheimer's disease patients, R3487 demonstrated a statistically significant effect on multiple measures of cognition.

Agents Associated with Tau or Alpha-Synuclein

Methylthioninium chloride, an inhibitor of tau protein aggregation is an example of an agent that is associated with tau or alpha-synuclein. Agents that may stabilize tau while part of the tubular nerve system may slow down the production of intra neuron fibrilary tangles and slow down the progression of the disease.

Agents that Regulate Amyloid Peptide Washout

Aβ-peptide specific antibodies, although they cannot penetrate the normal BBB, can cause equilibrium changes between the amount of Aβ oligomers in the brain, cerebrospinal fluid (CSF), and vascular system. The antibodies can bind and remove the Aβ peptide in CSF and blood and cause the equilibrium to favor washout of the Aβ peptide from brain. While many of these antibodies display significant toxicity and side effects, the toxicity is largely due to the large doses required.

Examples of Aβ-peptide specific antibodies include: bapineuzumab (Elan/Johnson & Johnson), solanezumab (LY2062430) (Eli Lilly), gammaglobulin IV (Baxter), and PF-4360365 (Pfizer).

ACC-001 (Elan/Johnson & Johnson) is an anti-beta amyloid vaccine; it stimulates the immune system to attack beta-amyloid.

Similarly, siRNA that targets Aβ peptide may be used. Some AD conditions and brain injury cause a breakdown in the BBB; therefore siRNA can penetrate the brain and silence Aβ peptide production.

CERE-110 (Ceregene Inc.) is nerve growth factor (NGF) gene therapy. NGF specifically targets basal forebrain cholinergic neurons, which release acetylcholine (Ach) in the cerebral cortex and hippocampus. Preclinical data in rats demonstrate that NGF prevented cholinergic neuron cell death and reversed age-related behavioral decline. NGF gene therapy has been tested in rhesus monkeys, and these studies demonstrated that NGF ameliorates cholinergic neuron atrophy and restores cholinergic axonal density in aged monkeys to levels observed in young monkeys.

Semagacestat (LY450139) is a gamma-secretase inhibitor; gamma secretase is responsible for proteolysis of amyloid precursor protein (APP). Proteolysis of APP forms Aβ.

Another gamma secretase inhibitor is NIC5-15 (Humanetics).

Therapeutic Methods

Combinations of the compounds described above may be administered to a subject in a single dosage form or by separate administration of each active agent. The agents may be formulated into a single tablet, pill, capsule, or solution for parenteral administration and the like. Individual therapeutic agents may be isolated from other therapeutic agent(s) in a single dosage form. Formulating the dosage forms in such a way may assist in maintaining the structural integrity of potentially reactive therapeutic agents until they are administered. Therapeutic agents may be contained in segregated regions or distinct caplets or the like housed within a capsule. Therapeutic agents may also be provided in isolated layers in a tablet.

Alternatively, the therapeutic agents may be administered as separate compositions, e.g., as separate tablets or solutions. One or more active agent may be administered at the same time as the other active agent(s) or the active agents may be administered intermittently. The length of time between administrations of the therapeutic agents may be adjusted to achieve the desired therapeutic effect. In certain instances, one or more therapeutic agent(s) may be administered only a few minutes (e.g., about 1, 2, 5, 10, 30, or 60 min) after administration of the other therapeutic agent(s). Alternatively, one or more therapeutic agent(s) may be administered several hours (e.g., about 2, 4, 6, 10, 12, 24, or 36 h) after administration of the other therapeutic agent(s). In certain embodiments, it may be advantageous to administer more than one dosage of one or more therapeutic agent(s) between administrations of the remaining therapeutic agent(s). For example, one therapeutic agent may be administered at 2 hours and then again at 10 hours following administration of the other therapeutic agent(s). The therapeutic effects of each active ingredient should overlap for at least a portion of the duration, so that the overall therapeutic effect of the combination therapy is attributable in part to the combined or synergistic effects of the combination therapy.

The dosage of the active agents will generally be dependent upon a number of factors including pharmacodynamic characteristics of each agent of the combination, mode and route of administration of active agent(s), the health of the patient being treated, the extent of treatment desired, the nature and kind of concurrent therapy, if any, and the frequency of treatment and the nature of the effect desired. In general, dosage ranges of the active agents often range from about 0.001 to about 250 mg/kg body weight per day. For a normal adult having a body weight of about 70 kg, a dosage may range from about 0.1 to about 25 mg/kg body weight. However, some variability in this general dosage range may be required depending upon the age and weight of the subject being treated, the intended route of administration, the particular agent being administered and the like. Since two or more different active agents are being used together in a combination therapy, the potency of each agent and the interactive effects achieved using them together must be considered. Importantly, the determination of dosage ranges and optimal dosages for a particular mammal is also well within the ability of one of ordinary skill in the art having the benefit of the instant disclosure.

Dosage ranges for agents may be as low as 5 ng/d. In certain embodiments, about 10 ng/day, about 15 ng/day, about 20 ng/day, about 25 ng/day, about 30 ng/day, about 35 ng/day, about 40 ng/day, about 45 ng/day, about 50 ng/day, about 60 ng/day, about 70 ng/d, about 80 ng/day, about 90 ng/day, about 100 ng/day, about 200 ng/day, about 300 ng/day, about 400 ng/day, about 500 ng/day, about 600 ng/day, about 700 ng/day, about 800 ng/day, about 900 ng/day, about 1 µg/day, about 2 µg/day, about 3 µg/day, about 4 µg/day, about 5 µg/day, about 10 µg/day, about 15 µg/day, about 20 µg/day, about 30 µg/day, about 40 µg/day, about 50 µg/day, about 60 µg/day, about 70 µg/day, about 80 µg/day, about 90 µg/day, about 100 µg/day, about 200 µg/day, about 300 µg/day, about 400 µg/day, about 500 µg/day, about 600 µg/day, about 700 µg/day, about 800 µg/day, about 900 µg/day, about 1 mg/day, about 2 mg/day, about 3 mg/day, about 4 mg/day, about 5 mg/day, about 10 mg/day, about 15 mg/day, about 20 mg/day, about 30 mg/day, about 40 mg/day, or about 50 mg/day of an agent of the invention is administered.

In certain embodiments, the agents of the invention are administered in pM or nM concentrations. In certain embodiments, the agents are administered in about 1 pM, about 2 pM, about 3 pM, about 4 pM, about 5 pM, about 6 pM, about 7 pM, about 8 pM, about 9 pM, about 10 pM, about 20 pM, about 30 pM, about 40 pM, about 50 pM, about 60 pM, about 70 pM, about 80 pM, about 90 pM, about 100 pM, about 200 pM, about 300 pM, about 400 pM, about 500 pM, about 600 pM, about 700 pM, about 800 pM, about 900 pM, about 1 nM, about 2 nM, about 3 nM, about 4 nM, about 5 nM, about 6 nM, about 7 nM, about 8 nM, about 9 nM, about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, or about 900 nM concentrations.

In certain embodiments, the size of the active agent is important. In certain embodiments, the active agent is less than about 3 µm, less than about 2 µm, less than about 1 µm in diameter. In certain embodiments, the active agent is from about 0.1 µm to about 3.0 µm in diameter. In certain embodiments, the active agent is from about 0.5 µm to about 1.5 µm in diameter. In certain embodiments, the active agent is about 0.2 µm, about 0.3 µm, about 0.4 µm, about 0.5 µm, about 0.6 µm, about 0.7 µm, about 0.8 µm, about 0.9 µm, about 1.0 µm, about 1.1 µm, about 1.2 µm, about 1.3 µm, about 1.4 µm, or about 1.5 µm in diameter.

It may be advantageous for the pharmaceutical combination to be comprised of a relatively large amount of the first component compared to the second component. In certain instances, the ratio of the first active agent to second active agent is about 200:1, 190:1, 180:1, 170:1, 160:1, 150:1, 140:1, 130:1, 120:1, 110:1, 100:1, 90:1, 80:1, 70:1, 60:1, 50:1, 40:1, 30:1, 20:1, 15:1, 10:1, 9:1, 8:1, 7:1, 6:1, or 5:1. It further may be preferable to have a more equal distribution of pharmaceutical agents. In certain instances, the ratio of the first active agent to the second active agent is about 4:1, 3:1, 2:1, 1:1, 1:2, 1:3, or 1:4. It also may be advantageous for the pharmaceutical combination to have a relatively large amount of the second component compared to the first component. In certain instances, the ratio of the second active agent to the first active agent is about 30:1, 20:1, 15:1, 10:1, 9:1, 8:1, 7:1, 6:1, or 5:1. In certain instances, the ratio of the second active agent to first active agent is about 100:1, 90:1, 80:1, 70:1, 60:1, 50:1, or 40:1. In certain instances, the ratio of the second active agent to first active agent is about 200:1, 190:1, 180:1, 170:1, 160:1, 150:1, 140:1, 130:1, 120:1, or 110:1. A composition comprising any of the above-identified combinations of first therapeutic agent and second therapeutic agent may be administered in divided doses about 1, 2, 3, 4, 5, 6, or more times per day or in a form that will provide a rate of release effective to attain the desired results. The dosage form may contain both the first and second active agents. The dosage form may be administered one time per day if it contains both the first and second active agents.

For example, a formulation intended for oral administration to humans may contain from about 0.1 mg to about 5 g of the first therapeutic agent and about 0.1 mg to about 5 g of the second therapeutic agent, both of which are compounded with an appropriate and convenient amount of carrier material varying from about 5 to about 95 percent of the total composition. Unit dosages will generally contain between about 0.5 mg to about 1500 mg of the first therapeutic agent and 0.5 mg to about 1500 mg of the second therapeutic agent. The dosage may be about 25 mg, 50 mg, 100 mg, 200 mg, 300 mg, 400 mg, 500 mg, 600 mg, 800 mg, or 1000 mg, etc., up to about 1500 mg of the first therapeutic agent. The dosage may be about 25 mg, 50 mg, 100 mg, 200 mg, 300 mg, 400 mg, 500 mg, 600 mg, 800 mg, or 1 000 mg, etc., up to about 1500 mg of the second therapeutic agent.

Definitions

As used herein, the following terms and phrases should have the meanings provided below.

The indefinite articles "a" and "an," as used herein in the specification and in the claims, unless clearly indicated to the contrary, should be understood to mean "at least one."

An "amyloidosis-associated condition" is a disease that is associated with amyloid deposition and can include but not be limited to Alzheimer's Disease, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, medullary carcinoma of the thyroid, isolated atrial amyloid, $P_2$-microglobulin amyloid in dialysis patients, inclusion body myositis, $\beta_2$-amyloid deposits in muscle wasting disease, and Islets of Langerhans diabetes Type I1 insulinoma. Type 2 diabetes mellitus, hereditary cerebral hemorrhage amyloidosis (Dutch), amyloid A (reactive), secondary amyloidosis, familial Mediterranean fever, familial amyloid nephropathy with urticaria and deafness (Muckle-wells Syndrome), amyloid lambda L-chain or amyloid kappa L-chain (idiopathic, myeloma or macroglobulinemia-associated) A beta 2M (chronic hemodialysis), ATTR (familial amyloid polyneuropathy (Portuguese, Japanese, Swedish)), familial amyloid cardiomyopathy (Danish), isolated cardiac amyloid, systemic senile amyloidoses, AIAPP or amylin insulinoma, atrial naturetic factor (isolated atrial amyloid), procalcitonin (medullary carcinoma of the thyroid), gelsolin (familial amyloidosis (Finnish)), cystatin C (hereditary cerebral hemorrhage with amyloidosis (Icelandic)), AApo-A-1 (familial amyloidotic polyneuropathy-Iowa), AApo-A-II (accelerated senescence in mice), head injuries (traumatic brain injury), dementia, fibrinogen-associated amyloid; and Asor or Pr P-27 (scrapie, Creutzfeld Jacob disease, Gertsmann-Straussler-Scheinker syndrome, bovine spongiform encephalitis) or in cases of persons who are homozygous for the apolipoprotein E4 allele, and the condition associated with homozygosity for the apolipoprotein E4 allele or Huntington's disease.

"Amyloidosis" is a condition characterized by the accumulation of various insoluble, fibrillar proteins in the tissues of a patient. An amyloid deposit is formed by the aggregation of amyloid proteins, followed by the further combination of aggregates and/or amyloid proteins.

Many forms of amyloidosis exist, and the disease can be classified into four groups: primary amyloidosis, secondary amyloidosis, hereditary amyloidosis, and amyloidosis associated with normal aging. Primary amyloidosis (light chain amyloidosis) occurs with abnormalities of plasma cells, and some people with primary amyloidosis also have multiple myeloma (cancer of the plasma cells). Typical sites of amyloid buildup in primary amyloidosis are the heart, lungs, skin, tongue, thyroid gland, intestines, liver, kidneys, and blood vessels. Secondary amyloidosis may develop in response to various diseases that cause persistent infection or inflammation, such as tuberculosis, rheumatoid arthritis, and familial Mediterranean fever. Typical sites of amyloid buildup in secondary amyloidosis are the spleen, liver, kidneys, adrenal glands, and lymph nodes. Hereditary amyloidosis has been noted in some families, particularly those from Portugal, Sweden, and Japan. The amyloid-producing defect occurs because of mutations in specific proteins in the blood. Typical sites for amyloid buildup in hereditary amyloidosis are the nerves, heart, blood vessels, and kidneys.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The terms "augmentation" or "augment" refer to combinations where one of the compounds increases or enhances therapeutic effects of another compound or compounds administered to a patient. In some instances, augmentation can result in improving the efficacy, tolerability, or safety, or any combination thereof, of a particular therapy.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The definition of each expression, e.g., alkyl, m, n, and the like, when it occurs more than once in any structure, is intended to be independent of its definition elsewhere in the same structure.

A comprehensive list of the abbreviations utilized by organic chemists of ordinary skill in the art appears in the first issue of each volume of the Journal of Organic Chemistry; this list is typically presented in a table entitled Standard List of Abbreviations.

The terms "hydroxy" and "hydroxyl" refer to the group —OH.

The term "oxo" refers to the group =O.

The term "carboxylate" or "carboxyl" refers to the group —COO⁻ or —COOH.

The term "cyano" refers to the group —CN.

The term "nitro" refers to the group —NO$_2$.

The term "amino" refers to the group —NH$_2$.

The term "acyl" or "aldehyde" refers to the group —C(=O)H.

The term "amido" or "amide" refers to the group —C(O)NH$_2$.

The term "aminoacyl" or "acylamino" refers to the group —NHC(O)H.

The term "thiol" refers to the group —SH.

The term "thioxo" refers to the group =S.

The term "sulfinyl" refers to the group —S(=O)H.

The term "sulfonyl" refers to the group —SO$_2$H.

The term "sulfonylamido" or "sulfonamide" refers to the group —SO$_2$NH$_2$.

The term "sulfonate" refers to the group SO$_3$H and includes groups having the hydrogen replaced with, for example a C$_{1-6}$alkyl group ("alkylsulfonate"), an aryl ("arylsulfonate"), an aralkyl ("aralkylsulfonate") and so on. C$_{1-3}$sulfonates are preferred, such as for example, SO$_3$Me, SO$_3$Et and SO$_3$Pr.

The term "isomers", as used herein, refer to stereoisomers, diastereomers, enantiomers and tautomers. "Tautomers" may be isomers that are readily interconvertable by rapid equilibrium. For example, carbonyl compounds that have a hydrogen on their alpha-carbon are rapidly interconverted with their corresponding enols.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

The term "heterocyclic" includes cycloalkyl or cycloalkenyl non-aromatic rings or ring systems that contain at least one ring heteroatom (e.g., O, S, N).

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are difluoromethyl, trifluoromethyl, and the like. "Halogens" are elements including chlorine, bromine, fluorine, and iodine.

The term "aryl" as used herein includes monocyclic or polycyclic aromatic hydrocarbons or ring systems. Examples of aryl groups include phenyl, naphthyl, biphenyl, fluorenyl and indenyl. Aryl groups may be substituted or unsubstituted. Aryl groups include aromatic annulenes, fused aryl groups, and heteroaryl groups. Aryl groups are also referred to herein as aryl rings.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno.

The term "annulene" refers to aryl groups that are completely conjugated monocyclic hydrocarbons. Examples of annulenes include cyclobutadiene, benzene, and cyclooctatetraene. Annulenes present in an aryl group will typically have one or more hydrogen atoms substituted with other atoms such as carbon.

When a group is present more than once in any formula or scheme described herein, each group (or substituent) is independently selected, whether explicitly stated or not. For example, for the formula —C(O)NR$_2$ each of the two R groups is independently selected.

As a means of simplifying the discussion and the recitation of certain terminology used throughout this application, the terms "group" and "moiety" are used to differentiate between chemical species that allow for substitution or that may be substituted and those that, in the particular embodiment of the invention, do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Pharmaceutically acceptable" as used herein means that the compound or composition or carrier is suitable for administration to a subject to achieve the treatments described herein, without unduly deleterious side effects in light of the necessity of the treatment.

The term "therapeutically effective amount" or "pharmaceutically appropriate dosage", as used herein, refers to the amount of the compounds or dosages that will elicit the biological or medical response of a subject, tissue or cell that is being sought by the researcher, veterinarian, medical doctor or other clinician.

As used herein, "pharmaceutically-acceptable carrier" includes any and all dry powder, solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The term "administering" or "administration", as used herein, refers to providing the compound or pharmaceutical composition of the invention to a subject suffering from or at risk of the diseases or conditions to be treated or prevented.

The term "systemic delivery", as used herein, refers to any suitable administration methods which may delivery the compounds in the present invention systemically. In one embodiment, systemic delivery may be selected from the group consisting of oral, parenteral, intranasal, inhaler, sublingual, rectal, and transdermal administrations.

A route of administration in pharmacology and toxicology is the path by which a drug, fluid, poison, or other substance is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract).

A topical administration emphasizes local effect, and substance is applied directly where its action is desired. Sometimes, however, the term topical may be defined as applied to a localized area of the body or to the surface of a body part, without necessarily involving target effect of the substance, making the classification rather a variant of the classification based on application location. In an enteral administration, the desired effect is systemic (non-local), substance is given via the digestive tract. In a parenteral administration, the desired effect is systemic, and substance is given by routes other than the digestive tract.

The examples for topical administrations may include epicutaneous (application onto the skin), e.g., allergy testing or typical local anesthesia, inhalational, e.g. asthma medications, enema, e.g., contrast media for imaging of the bowel, eye drops (onto the conjunctiva), e.g., antibiotics for conjunctivitis, ear drops, such as antibiotics and corticosteroids for otitis externa, and those through mucous membranes in the body.

Enteral administration may be administration that involves any part of the gastrointestinal tract and has systemic effects. The examples may include those by mouth (orally), many drugs as tablets, capsules, or drops, those by gastric feeding tube, duodenal feeding tube, or gastrostomy, many drugs and enteral nutrition, and those rectally, various drugs in suppository.

The examples for parenteral administrations may include intravenous (into a vein), e.g. many drugs, total parenteral nutrition intra-arterial (into an artery), e.g., vasodilator drugs in the treatment of vasospasm and thrombolytic drugs for treatment of embolism, intraosseous infusion (into the bone marrow), intra-muscular, intracerebral (into the brain parenchyma), intracerebroventricular (into cerebral ventricular system), intrathecal (an injection into the spinal canal), and subcutaneous (under the skin). Among them, intraosseous infusion is, in effect, an indirect intravenous access because the bone marrow drains directly into the venous system. Intraosseous infusion may be occasionally used for drugs and fluids in emergency medicine and pediatrics when intravenous access is difficult.

Any route of administration may be suitable for the present invention. In one embodiment, the compound of the present invention may be administered to the subject via intravenous injection. In another embodiment, the compounds of the present invention may be administered to the subject via any other suitable systemic deliveries, such as oral, parenteral, intranasal, sublingual, rectal, or transdermal administrations.

In another embodiment, the compounds of the present invention may be administered to the subject via nasal systems or mouth through, e.g., inhalation.

In another embodiment, the compounds of the present invention may be administered to the subject via intraperitoneal injection or IP injection.

As used herein, the term "intraperitoneal injection" or "IP injection" refers to the injection of a substance into the peritoneum (body cavity). IP injection is more often applied to animals than to humans. In general, IP injection may be preferred when large amounts of blood replacement fluids are needed, or when low blood pressure or other problems prevent the use of a suitable blood vessel for intravenous injection.

In animals, IP injection is used predominantly in veterinary medicine and animal testing for the administration of systemic drugs and fluids due to the ease of administration compared with other parenteral methods.

In humans, the method of IP injection is widely used to administer chemotherapy drugs to treat some cancers, in particular ovarian cancer. Although controversial, this specific use has been recommended as a standard of care.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

As used herein, the term "subject" or "individual" refers to a human or other vertebrate animal. It is intended that the term encompass "patients."

The term "synergistic" refers to a combination which is more effective than the additive effects of any two or more single agents. A synergistic effect permits the effective treatment of a disease using lower amounts (doses) of individual therapy. The lower doses result in lower toxicity without reduced efficacy. In addition, a synergistic effect can result in improved efficacy. Finally, synergy may result in an improved avoidance or reduction of disease as compared to any single therapy.

Combination therapy can allow for the product of lower doses of the first therapeutic or the second therapeutic agent (referred to as "apparent one-way synergy" herein), or lower doses of both therapeutic agents (referred to as "two-way synergy" herein) than would normally be required when either drug is used alone.

As used herein, "pharmaceutically-acceptable carrier" includes any and all solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The formulation used in the present invention may also contain stabilizers, preservatives, buffers, antioxidants, or other additives known to those of skill in the art. The use of such media and agents for pharmaceutically-active substances is well known in the art. Supplementary active compounds can also be incorporated into the imaging agent of the invention. The imaging agent of the invention may further be administered to an individual in an appropriate diluent or adjuvant, co-administered with enzyme inhibitors or in an appropriate carrier such as human serum albumin or liposomes. Pharmaceutically-acceptable diluents include sterile saline and other aqueous buffer solutions. Adjuvants contemplated herein include resorcinols, non-ionic surfactants such as polyoxyethylene oleyl ether and n-hexadecyl polyethylene ether. Enzyme inhibitors include pancreatic trypsin inhibitor, diethylpyrocarbonate, and trasylol. Liposomes inhibitors include water-in-oil-in-water CGF emulsions, as well as conventional liposomes (see *J. Neuroimmunol.* 1984, 7, 27).

As described herein, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. See *J. Pharm. Sci.* 1977, 66, 1-19.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, *J. Pham. Sci.* 1977, supra)

More specifically, the compounds that can be formulated into a pharmaceutical composition include a therapeutically-effective amount of the first compound, a therapeutically effective amount of the second compound, and a pharmaceutically-acceptable carrier. The therapeutically-effective amount of the compounds and the specific pharmaceutically-acceptable carrier will vary depending upon, e.g., the age, weight, sex of the subject, the mode of administration, and the type of viral condition being treated.

In a particular aspect, the pharmaceutical composition which can be used includes the compounds of the present invention in effective unit dosage form. As used herein, the term "effective unit dosage" or "effective unit dose" is used herein to mean a predetermined amount sufficient to be effective against AD or the like. Examples include amounts that enable treatment of amyloid deposit(s) in vivo or in vitro that yield acceptable toxicity and bioavailability levels for pharmaceutical use, and/or prevent cell degeneration and toxicity associated with fibril formation.

The pharmaceutical compositions may contain the first compound or the second compound used in the method of this invention in an amount of from 0.01 to 99% by weight of the total composition, preferably 0.1 to 80% by weight of the total composition. For oral administration, the first compound or the second compound is generally administered in an amount of 0.1 g/body to 15 g/body, preferably 0.5 g/body to 5 g/body. For intravenous injection, the dose may be about 0.1 to about 30 mg/kg/day, preferably about 0.5 to about 10 mg/kg/day. If applied topically as a liquid, ointment, or cream, the first compound or the second compound may be present in an amount of about 0.1 to about 50 mg/mL, preferably about 0.5 to 30 mg/mL of the composition.

For systemic administration, the daily dosage as employed for adult human treatment will range from about 0.1 mg/kg to about 150 mg/kg, preferably about 0.2 mg/kg to about 80 mg/kg.

All of the U.S. patents and U.S. patent application publications cited herein are hereby incorporated by reference.

Those skilled in the art will recognize, or be able to ascertain using no more than routine experimentation, many equivalents to the specific embodiments of the invention described herein. Such equivalents are intended to be encompassed by the following claims.

EXAMPLES

It should be understood that the above-described embodiments and the following examples are given by way of illustration, not limitation. Various changes and modifications within the scope of the present invention will become apparent to those skilled in the art from the present description.

Example 1

Cromolyn and Ibuprofen Combination Treatment

The following is a dosing example calculation for cromolyn:
1. Effective comolyn administration for AD treatment is significantly different from that of cromolyn for lung inflammation and asthma. For lung inflammation or asthma subjects use inhalation devices 1-4 times per day; each inhaled dose contains 20 mg of dry powder.
2. The dry cromolyn powder (usual size is >5 microns) is formulated with lactose with much larger size.
3. When inhaled, dry cromolyn powder is separated from the lactose via the inhaler device action (spinhaler, cyclohaler, or monodose inhalers) or in the upper part of the airway and the dry cromolyn is delivered to the lung.
4. Cromolyn has also been delivered as a solution that enters via the gastric system.

For AD, these treatments will not result in any significant action on AD progression or modification.

For AD treatment, to be effective, the drug has to be delivered systemically to allow for brain uptake. Therefore, cromolyn dry powder has to be <3 microns. In certain embodiments, cromolyn is from about 0.5 microns to about 1.5 microns in diameter. Powders of this size will reach the alvular nodes and be delivered systemically.

The estimated dose for daily treatment is about 16 mg per subject per day, about 4 mg per subject per day, or about 1 mg per subject per day.

From a preliminary biodistribution of a cromolyn analog labeled with F-18, the brain uptake is about 1% dose per gram in the brain. Therefore, it is estimated that from a 16 mg dose, for 1 mg taken systematically, 0.01 mg will be taken in the brain. The estimated dose per gram of brain will be 0.01/1500 gram (average brain mass); this equals 7 ng/gram of brain. This amount slows down polymerization of the daily Aβ peptide produced in the brain. Therefore, amounts that are 5 times lower than the 80 mg used for asthma treatment, should be effective. Cromolyn has a Log P of 1.9, PSA of 189, and % PSA of 44 (JOURNAL OF PHARMACEUTICAL SCIENCES, VOL. 92, NO. 6, JUNE 2003).

Inhibition data showed that cromolyn inhibits Aβ peptide polymerization by 8 fold. Other inhibition experiments showed that cromolyn inhibits Aβ peptide polymerization in 5 nM concentrations.

In combination with cromolyn, a dose of 2 mg of ibuprofen could be given as pill, capsule, or liquid. This low dose of ibuprofen is sufficient to treat the invisible inflammation response to the Aβ peptide. Higher doses may work initially but may worsen the AD subjects in the long run.

Example 2

In Vivo Experiments of Cromolyn and Ibuprofen Combination Treatment

Three mice groups (five animals in each) were tested in a Morris water navigation test. Two groups were four months young APP/PS1 including a mutant Aβ mouse and a model indicative of Alzheimer's Disease progression. One APP/PS1 group was treated with Cromolyn and ibuprofen combination for six months, and the second was untreated as an control group and a third untreated wild type was used as a normal control. FIG. 1 is a graph showing the in-vivo study summary. WT (wild type, right panel) shows normal untreated mice. The control group (left panel) shows transgenic mice that did not received drug treatment. The treated group (Mid panel) shows transgenic mice that received AZLT-OP1(cromolyn+ibuprofen) for six month by Intraperitoneal (IP) injection twice weekly. Mice were trained for 7 days to remember the location of the platform. At day 8, the platform was removed, and the times of crossing the platform area was recorded.

Figure 4:
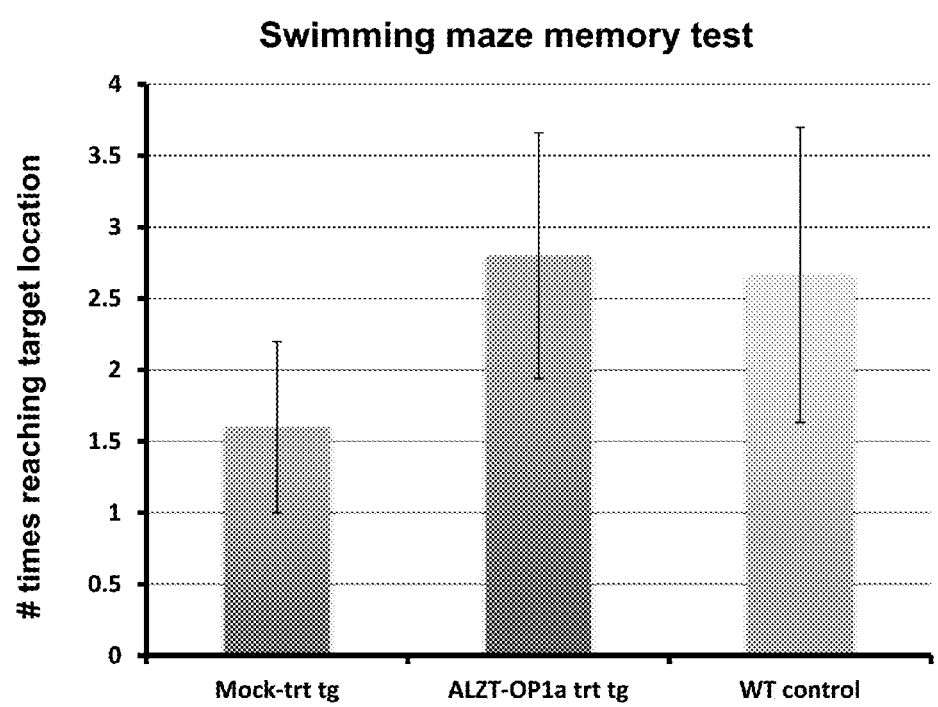
FIG. 4 depicts the water maze recorded data of in vivo cromolyn and ibuprofen treatment of transgenic mice-modeling like Alzheimer's Disease. The results indicate that treated transgenic mice have closely behavior to wild type normal control group.

In another study, 7.5 month old APP/PS1 mice completed treated for a week as an acute treatment using three different doses of Cromolyn Sodium (1.05 mg/kg, 2.1 mg/kg and 3.15 mg/kg). The treatment was given by IP injection everyday for 7 days before sacrificing the mice and harvesting the brain. Brain extracts were quantified for the total amount of Aβ40, Aβ42 and Aβ oligomers. FIG. 4 depicts the results of in vivo cromolyn and ibuprofen treatment of transgenic mice modeling like Alzheimer' Disease.

Here are the main conclusions of this acute study:
1. A dose-dependent decrease in the amount of Aβ40 and Aβ42 associated with the two higher doses (2.1 mg/kg and 3.15 mg/kg), up to 50% was observed.
2 This effect was sustained after treatment of the samples with guanidine-HCl to dissolve any amyloid aggregates.
3 The quantification of oligomeric species using the 82E1/82E1 ELISA kit failed to show any difference among the experimental groups.

One explanation to the insignificant change is that acute exposure to Cromolyn Sodium treatment primarily affects monomeric species, impacting oligomers or higher-order aggregates chronic longer treatment term. Acute treatment would not cause a substantial change in the oligomeric quantities.

Example 3

Cromolyn Derivatives for Inhibiting Polymerization of Alzheimer's Disease Oligomers and Treating Alzheimer's Disease In another experiment, cromolyn derivatives were tested as inhibitors of Aβ polymerization. Inhibiting Aβ oligomer production will provide of Alzheimer's Disease and treating Alzheimer's Disease.

The investigational product ALZT-OP1a (cromolyn sodium) is a synthetic chromone derivative that has been approved for use by the FDA since the 1970s for the treatment of asthma. For asthma treatment, cromolyn sodium powder was micronized for inhalation to the lungs via dry powder inhaler, i.e. the Spinhaler device. Liquid intranasal and ophthalmic formulations have also been developed for the treatment of rhinitis and conjunctivitis.

The mechanism of action for cromolyn sodium (ALZT-OP1a) is characterized as a mast cell stabilizer, namely to suppress cytokine release from activated lymphocytes together with preventing the release of histamine from mast cells (Netzer, 2012; Keller, 2011). It was administered four times daily as prophylaxis for allergic and exercise-induced asthma, not as a treatment for acute attacks.

Applicants have discovered a new mechanism of action for cromolyn, which, along with its role for suppressing immune responses, enables the re-purposing of this approved drug for use to halt AD progression. The Applicants' studies have shown that cromolyn sodium binds to beta-amyloid peptides and inhibits its polymerization into oligomers and higher order aggregates. The inhibition of beta-amyloid polymerization will arrest amyloid-mediated intoxication of neurons and restore the passage of these aberrant beta-amyloid oligomers out of the brain rather than their accumulation.

Applicants' studies showed that cromolyn or its derivatives penetrates the blood-brain barrier in animal models, so that plasma bioavailability following cromolyn inhalation will translate to concentrations in the brain sufficient to interfere with beta-amyloid oligomerization and accumulation. Inhalation of cromolyn sodium was shown to be the most effective non-injected administration route for systemic bioavailability of cromolyn sodium in animals and humans (Moss, 1970; Neale, 1986; Richards, 1987; Aswania, 1999; Tronde, 2003). An FDA-approved route of administration for cromolyn sodium is oral inhalation using a capsule-based dry powder inhaler, with 20 mg cromolyn sodium loaded per capsule. Studies have shown that with high inspiratory rates, the inhaled cromolyn sodium is delivered efficiently to the human lung, with 10-15% of the inhaled drug-delivered-dose absorbed into the bloodstream (Richards, 1987; Keller, 2011). For these reasons, cromolyn sodium inhalation with a dry powder inhaler device was selected as the route of administration in the present invention. However, plasma levels of cromolyn following inhalation are reported to show high intra- and inter-subject variability, and that cromolyn uptake by asthmatics was lower than in healthy volunteers (Richards, 1987; Keller, 2011).

For planned human studies, each blister will contain the active product ingredient (cromolyn sodium) and inhalation grade lactose monohydrate as an excipient. The once-daily cromolyn dose to be tested in this study is less than 20% the dose from the four-times daily approved dose level (80 mg cromolyn sodium total per day) for the treatment of asthma.

Taken together, the once daily ALZT-OP1a dose in this study should preserve the drug's excellent safety and tolerability profile, yet is predicted to achieve the nanomolar drug concentrations needed to block beta-amyloid oligomerization in the brain to prevent Alzheimer's disease progression.

Example 4

Figure 5A:
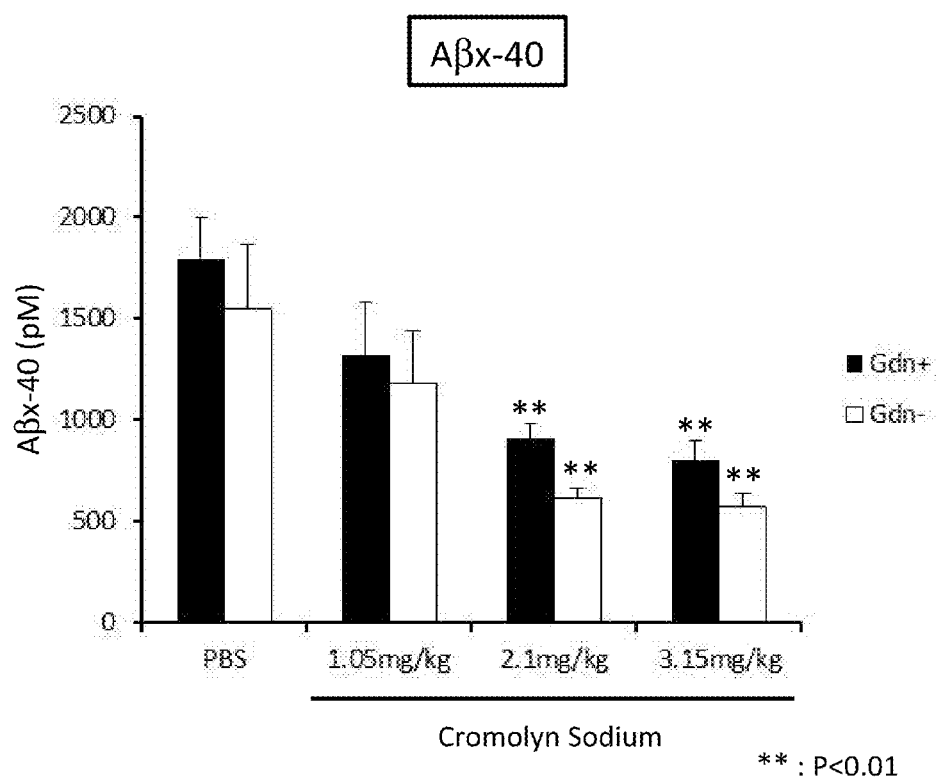
FIG. 5A illustrates the measurement of TBS soluble Aβ level by WAKO ELISA. The experiments show that TBS Aβ level decreases following by treatment of cromolyn sodium with dose-dependency and shows that Aβ-40 level decreases following by treatment of cromolyn sodium with dose-dependency.
Figure 5B:
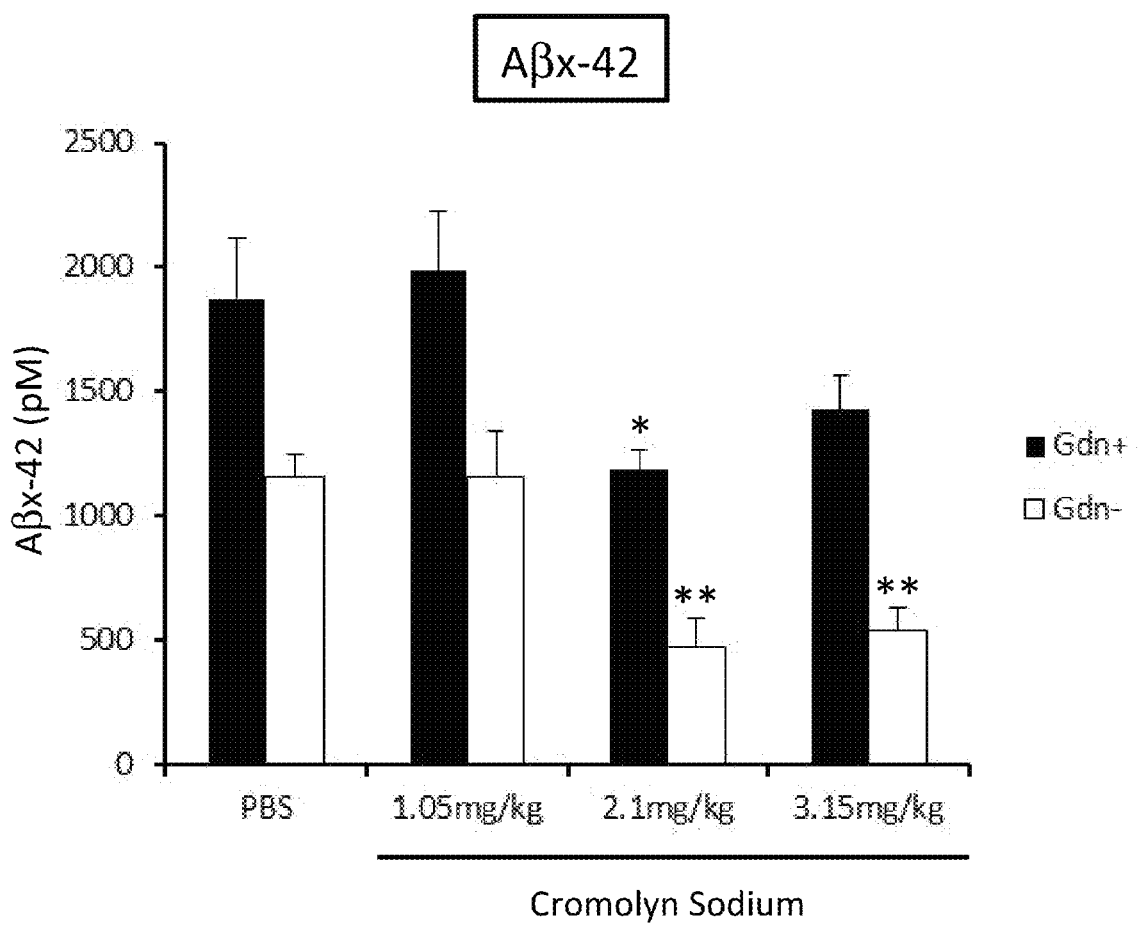
FIG. 5B illustrates the measurement of TBS soluble Aβ level by WAKO ELISA. The experiments show that TBS Aβ level decreases following by treatment of cromolyn sodium with dose-dependency and shows that Aβ-42 level decreases following by treatment of cromolyn sodium with dose-dependency. N=3 or 5 animals per group, average ±SE. The p value is significant using one-way ANOVA test (Bonferroni's test). Both of total soluble Aβ (as shown as Gdn+) and monomeric Aβ (as shown as Gdn−) decease after the addition of cromolyn sodium. The dose of 2.1 mg/kg of cromolyn sodium was enough to decrease TBS soluble Aβ.

Cromolyn Derivatives for Inhibiting Polymerization of Alzheimer's Disease Oligomers FIG. 5 illustrates the measurement of TBS soluble Aβ level by WAKO ELISA. The experiments show that TBS Aβ level decreases following by treatment of cromolyn sodium with dose-dependency. FIG. 5A shows that Aβ40 level decreases following by treatment of cromolyn sodium with dose-dependency. FIG. 5B shows that Aβ42 level decreases following by treatment of cromolyn sodium with dose-dependency. As indicated, the number of animals per group is N=3 or 5, average ±SE. The p value is significant using one-way ANOVA test (Bonferroni's test). Both of total soluble Aβ [as shown as Gdn+(Guanidine-HCl)] and monomeric Aβ [as shown as Gdn-(no guanidine)] decease after the addition of cromolyn sodium. The dose of 2.1 mg/kg of cromolyn sodium was enough to decrease TBS soluble Aβ.

Figure 6A:
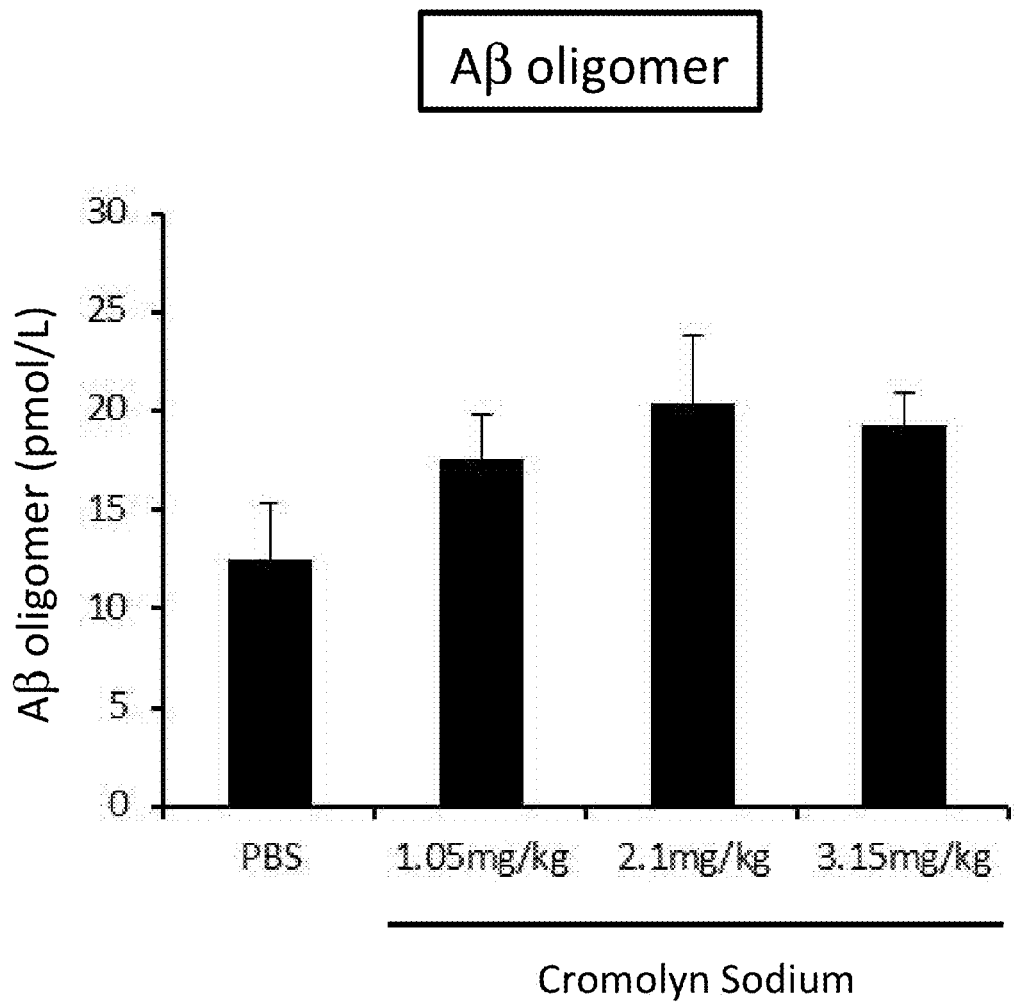
FIG. 6A illustrates the measurement of TBS soluble Aβ oligomer level IBL oligomer ELISA. The experiments show that Aβ oligomer level was not changed following the treatment with cromolyn sodium and shows the experiments of IBL Aβ oligomer ELISA (82E1-82E1).
Figure 6B:
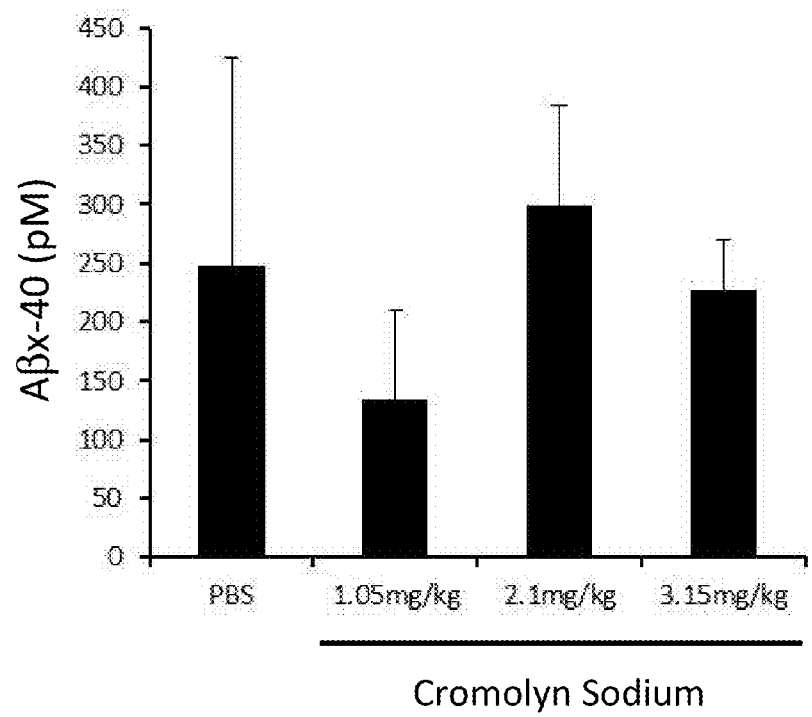
FIG. 6B illustrates the measurement of TBS soluble Aβ oligomer level IBL oligomer ELISA. The experiments show that Aβ oligomer level was not changed following the treatment with cromolyn sodium and show the difference the experiments with Gdn and those without Gdn using Aβ WAKO ELISA. N=3 or 5 animals per group, average ±SE. The p value is not significant using one-way ANOVA test (Bonferroni's test). Both ELISA (IBL oligomer ELISA and the differences between with and without Gdn using WAKO ELISA) showed that oligomer level was not changed following the treatment with cromolyn sodium.
Figure 6C:
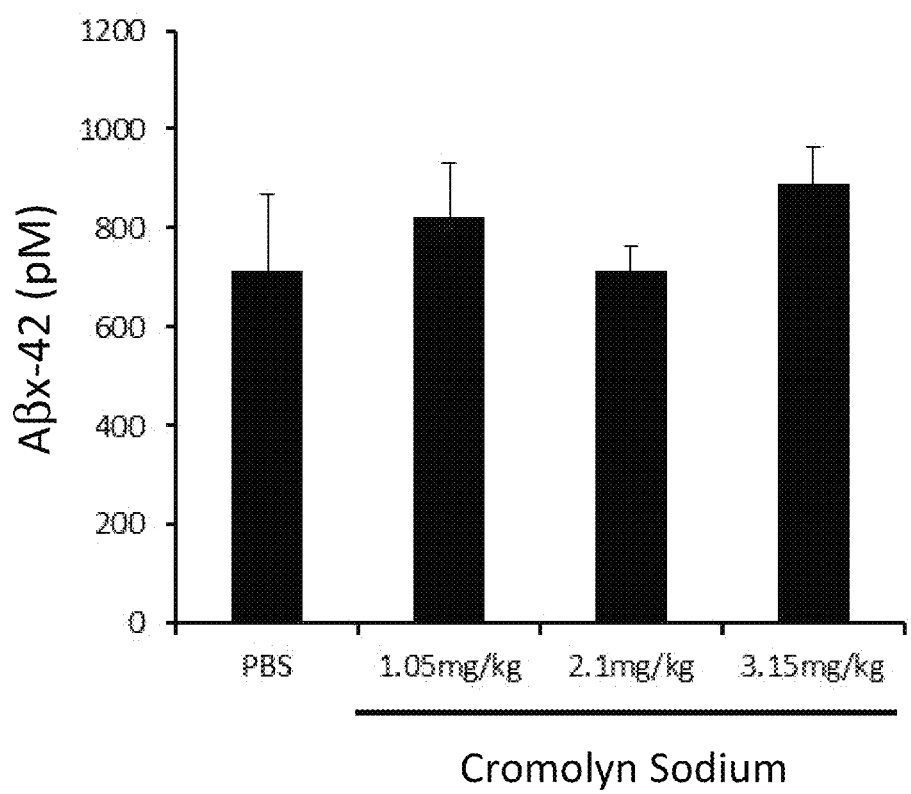
FIG. 6C illustrates the measurement of TBS soluble Aβ oligomer level IBL oligomer ELISA. The experiments show that Aβ oligomer level was not changed following the treatment with cromolyn sodium and show the difference the experiments with Gdn and those without Gdn using Aβ WAKO ELISA. N=3 or 5 animals per group, average ±SE. The p value is not significant using one-way ANOVA test (Bonferroni's test). Both ELISA (IBL oligomer ELISA and the differences between with and without Gdn using WAKO ELISA) showed that oligomer level was not changed following the treatment with cromolyn sodium.

FIG. 6 illustrates the measurement of TBS soluble Aβ oligomer level IBL oligomer ELISA (82E1-82E1). The experiments show that Aβ oligomer level was not changed following the treatment of cromolyn sodium. FIG. 6A shows the experiments of IBL Aβ oligomer ELISA (82E1-82E1). FIGS. 6B and 6C show the difference the experiments with Gdn and those without Gdn using Aβ WAKO ELISA. N=3 or 5 animals per group, average ±SE. The p value is not significant using one-way ANOVA test (Bonferroni's test). Both ELISA (IBL oligomer ELISA and the differences between with and without Gdn using WAKO ELISA) showed that oligomer level was not changed following the treatment of cromolyn sodium.

Example 5

Discussion

Applicants summarize the rationale behind the treatment as follows:
1. Molecular structure is similar to some that had affinity to plaque (Foruma I and table 1). The significant difference is that the drug in the present invention works in nanomolar concentrations as compared to micromolar concentrations of other previous drugs.

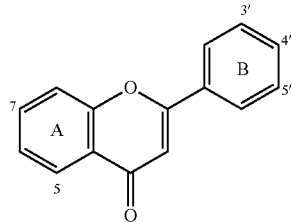

(I)

TABLE 1

The structural similarity of fisetin analogues and their effects on Aβ fibril formation.

| Compound | Substituents | | | | | | Effects on Aβ fibril formation |
|---|---|---|---|---|---|---|---|
| | 3 | 5 | 7 | 3' | 4' | 5' | |
| Fisetin | OH | H | OH | OH | OH | H | Inhibitory |
| 3,4',7-Tri-hydroxyflavone | H | H | OH | OH | OH | H | Inhibitory |

TABLE 1-continued

The structural similarity of fisetin analogues and their effects on Aβ fibril formation.

| Compound | Substituents | | | | | | Effects on Aβ fibril formation |
|---|---|---|---|---|---|---|---|
| | 3 | 5 | 7 | 3' | 4' | 5' | |
| 3,3',4'-Tri-hydroxyflavone | OH | H | H | OH | OH | H | Inhibitory |
| 3,3',7-Tri-hydroxyflavone | OH | H | OH | OH | H | H | Enhancing |
| 5-Deoxy-kaempferol | OH | H | OH | H | OH | H | Enhancing |
| Luteolin | H | OH | OH | OH | OH | H | Inhibitory |
| Quercetin | OH | OH | OH | OH | OH | H | Inhibitory |
| Chrysin | H | OH | OH | H | H | H | Enhancing |
| Kaempferol | OH | OH | OH | H | OH | H | Enhancing |
| Myricetin | OH | OH | OH | OH | OH | OH | Inhibitory |

2. The suitable molecular weight of the molecules in the present invention allows the molecules to penetrate brain.
Chemical Structure:

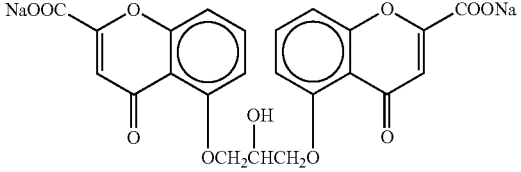

Molecular Formula: $C_{23}H_{14}Na_2O_{11}$
Molecular Weight: 512.34 [g/mol]

3. The molecules in the present invention have desirable lipophilicity (Log P) and pressure surface area (PSA) in the brain penetration range (Table 2). The PIB analog TS3124 has a 4% brain concentration, and a higher Log P value in a range that there is no usal uptake. This is balanced by the much lower PSA. Log P was determined by Chemdraw pro, Version 10. PSA was determined by the previous methods (http://www.daylight.com/meetings/emug00/Ert1/tpsa.html).

TABLE 2

The moelcular structures, molecular weight, lipophilicity (LogP) and pressure surface area (PSA).

| compound | Structure | Mw | logP | PSA | PKa |
|---|---|---|---|---|---|
| TS734 | (structure shown) | 466.41 | 2.1 | 127.20 | |
| C0399 | (structure shown) | 508.38 | 1.39 for diacid | 125.43 | |
| TS3124 | (structure shown) | 302.37 | 3.92 | 45.15 | OH:9.2 NH:19.2 |

Figure 7:
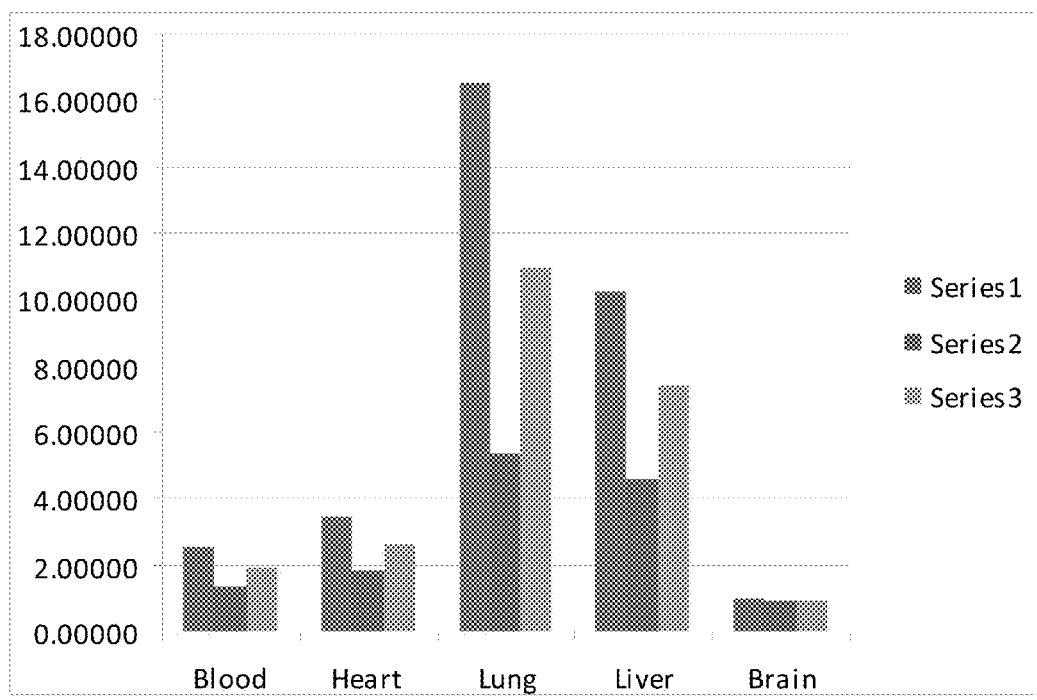
FIG. 7 illustrates the biodistribution of cromolyn Compound A following intravenous injection in mice.
Figure 8:
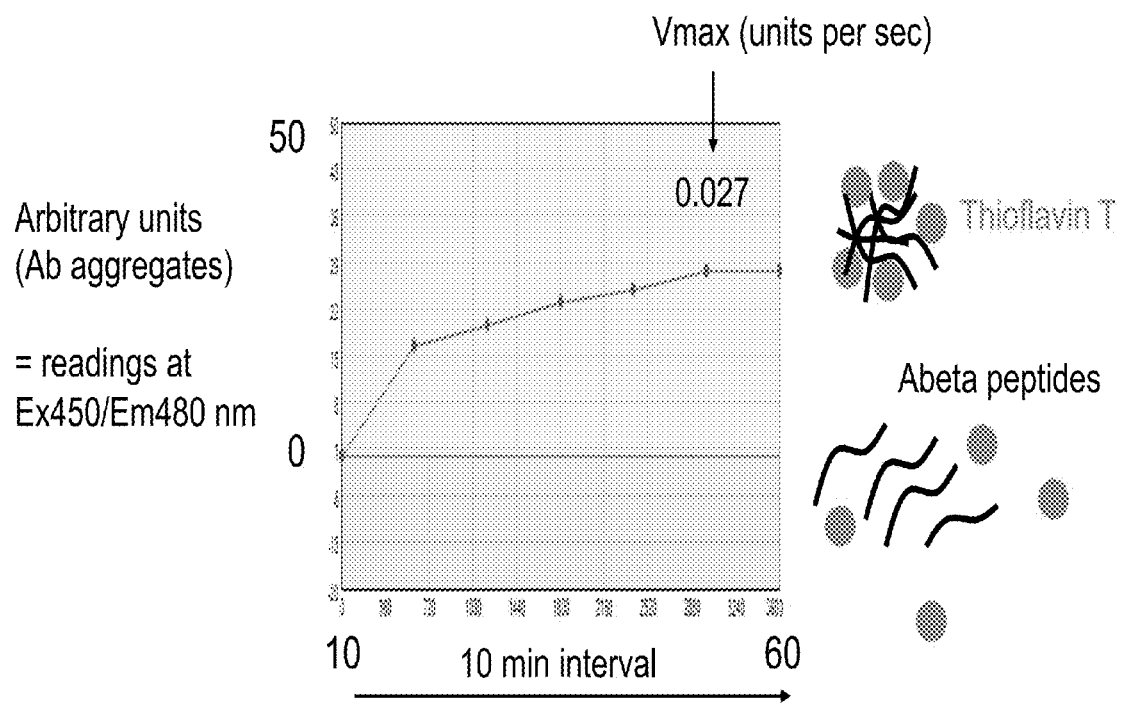
FIG. 8 illustrates Aβ aggregation test in the absence of cromolyn. The experiment was assayed by thioflavin fluorescent intensity kinetics.
Figure 9:
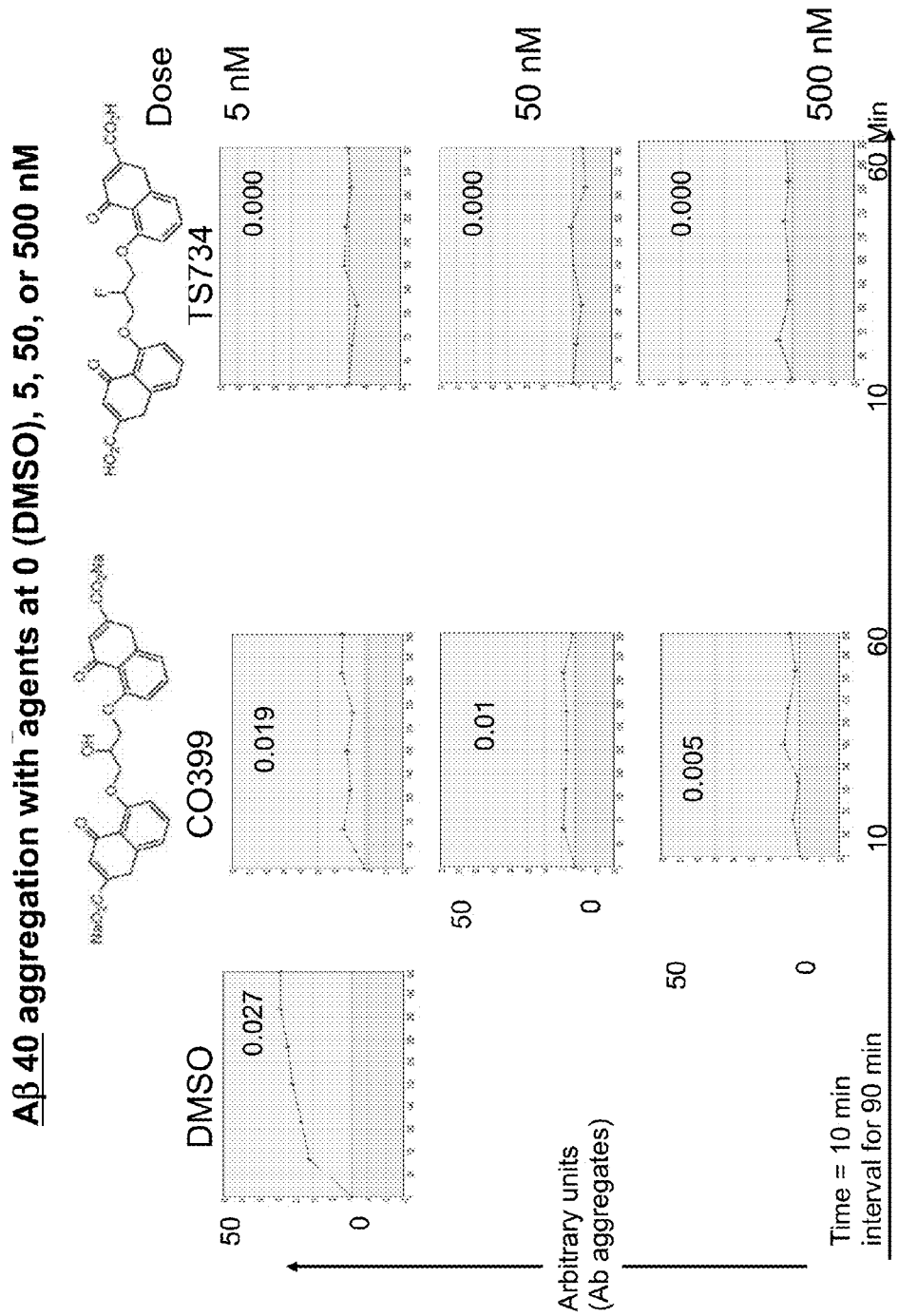
FIG. 9 illustrate Aβ aggregation test after the addition of cromolyn (CO399) or its $^{19}$F derivative (TS734). The addition of cromolyn (CO399) and its $^{19}$F derivative (TS734) at nanomolar concentration shows inhibition of Aβ aggregation.

4. Mice biodistribution of radiolabeled cromolyn biodistribution shows 1% dose per gram brain accumulate. FIG. 7 illustrates the biodistribution of radiolabeled cromolyn Compound A following intravenous injection in mice. In FIG. 7, a 5, 30 or 60 minute, corresponding to Series 1, 2 or 3, respectively in the graph, brain uptake shows 1% accumulation with little or no washout for the period measured.

5. The binding of cromolyn to Aβ and its polymerization inhibition was confirmed by four independent methods.

UV Aggregation Assay

Abeta peptide aggregation and the impact of drugs to slow or prevent Abeta aggregation was measured by a UV absorbance assay (Findeis, 1999). Abeta (1-40) peptides, at 50 µM, were mixed with 50 µM drug in assay buffer and the plate was incubated at ambient temperature on a plate reader. The UV absorbance was monitored at 540 nm over a 2-3 h period.

Polymerization of Aβ-monomer peptides into clusters of trimers and tetramers initiates the Aβ aggregation process into protofibrils and then into fibrils that form amyloid plaques. The polymerization experiments revealed that Aβ monomer reached 50% polymerization in 14 minutes. At equimolar concentrations with Aβ, the addition of cromolyn inhibited the rate of Aβ polymerization 7-fold, namely 50% polymerization required 75 minutes incubation, compared to 14 minutes in the absence of drug.

TABLE 3

Cromolyn inhibits Aβ polymerization.

| Test Compound | % Thioflavin T Bound | Relative Binding | Relative Increase in Polymerization Time (fold) |
|---|---|---|---|
| Vehicle | 37% | 1 | 1 |
| TS734 (cromlyn) | 30% | 0.82 | 7.8 |

LC/MS/MS Binding Assay

Binding was measured by equilibrium dialysis. Amyloid fibrils were preformed by incubating the peptide in buffer with shaking for 120 h at 27° C. The drugs were incubated with fibrils (50 µM peptide) in a RED equilibrium dialysis device (Pierce), and the amount of test agent on each side is determined by LC/MS/MS. Percent bound was calculated as 1−(free conc/total conc) after correcting for background signal. Thioflavin-T was used as a positive control. Binding is displacement of Thioflavin T. Polymerization is ranked for relative Aβ. In general, compounds that rank highly in inhibiting polymerization rank low in binding to aggregates, and vice versa.

Competition Binding Assay

The competition assay was performed as described previously (Ono and Hayashi, 2009). Amyloid peptide aggregates were preformed by incubating Aβ (1-40) peptide with buffer for 3 days at 37° C. Drugs at 20 µM were mixed with assay solution containing 10 µg/mL amyloid peptide aggregates+3 µM Thioflavin-T on one side of a RED dialysis device with assay buffer added to the other side. After 4 h dialysis, the amount of Thioflavin-T was determined by LC/MS/MS. The relative binding was determined by normalizing the percent binding by the percent binding of the vehicle control.

Aβ Aggregation by Thioflavin T Assay

One of the most routinely used approaches to monitor Aβ polymerization is the thioflavin T binding assay. When thioflavin T binds to beta-sheet rich structures, such as amyloid aggregates, the dye displays enhanced fluorescence and a characteristic red shift in its emission spectrum. Aβ peptide at 5 µM was mixed with 10 µM thioflavin T with drug at different concentrations. In the absence of drug, Aβ polymerization shows increasing thioflavin T fluorescence over 60-180 min, as shown in FIG. 5.

The addition of cromolyn (CO399) and its $^{18}$F derivative (TS734) at nanomolar concentration shows inhibition of Aβ aggregation, as shown in FIG. 6.

By four separate in vitro assays, cromolyn sodium, at nanomolar concentrations, effectively inhibits Aβ amyloid peptide polymerization into oligomers and higher order aggregates.

Figure 10:
FIG. 10 illustrates the side view of the relative structures and locations of cromolyn and Aβ after cromolyn binds Aβ through a binding model simulation.
Figure 11:
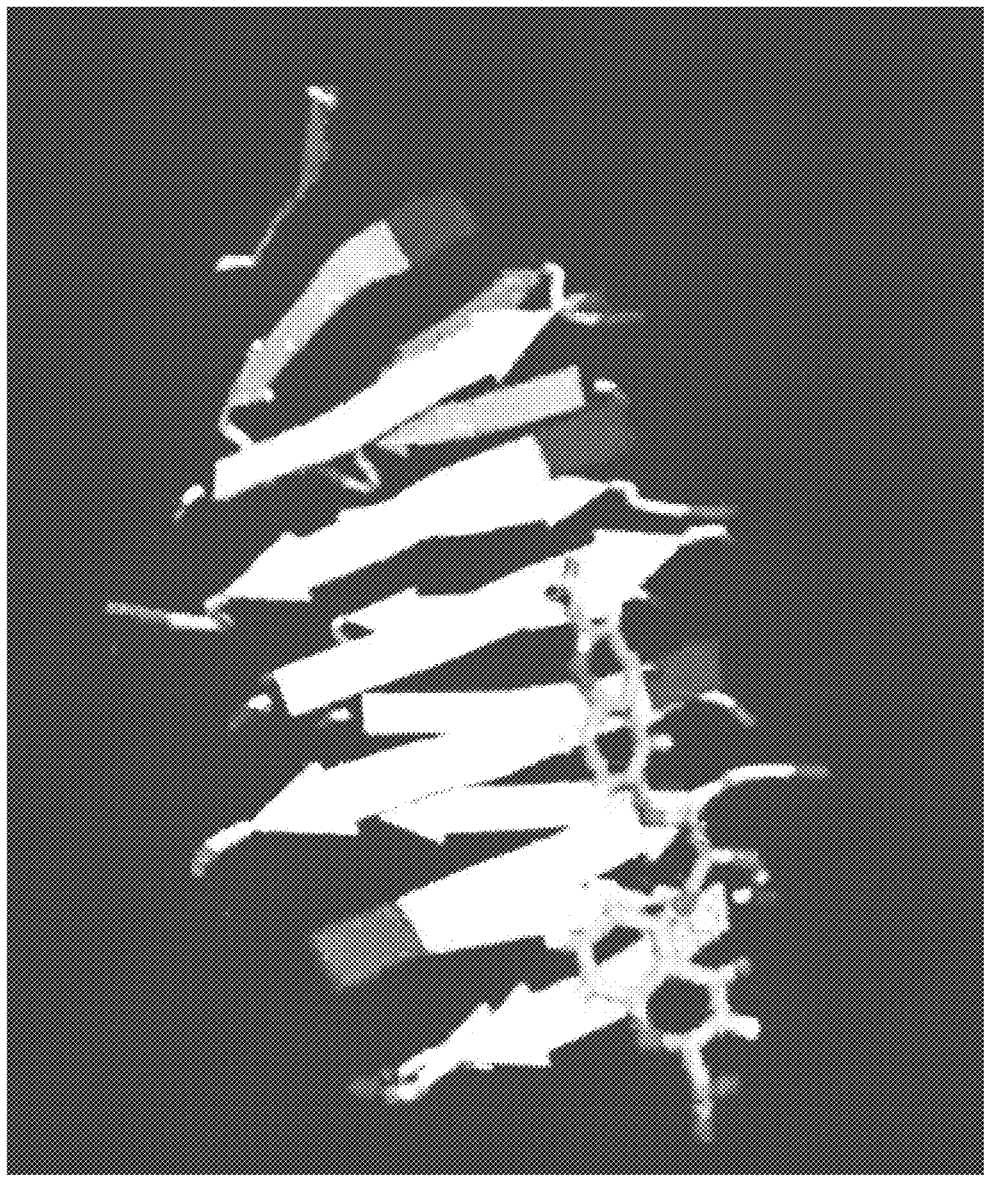
FIG. 11 illustrate the top view of the relative structures and locations of cromolyn and Aβ after cromolyn binds Aβ through a binding model simulation.

6. Preliminary analysis of the binding model indicates that cromolyn binding to the surface of beta sheet across the beta strand in a manner similar to Thioflavin-T. FIGS. 10 and 11 illustrate the side and top view of the relative structures and locations of cromolyn and Aβ after cromolyn binds Aβ through a binding model simulation.

7. Applicants tested several other structures for treating AD in addition to cromolyn. Several types of compounds for both imaging and therapeutic agents have been evaluated for Aβ peptide polymerization inhibition.

In an effort to combine bioavailability and dual function, Applicants have tethered scyllo-inositol, which is transported across the blood-brain barrier and known to bind and neutralize oligomers into soluble complexes (McLaurin, Kierstead, et al., 2006; Sun, Zhang, et al., 2008), to 2-ethyl-8-methyl-2,8-diazospiro-4,5-decan-1,3-dione, a muscarinic M1 receptor agonist (Palacios, Bolliger, et al., 1986). RS-86 was chosen because evidence has shown that it improves cognitive function, mood and social behavior in some AD patients (Wettstein and Spiegel, 1985). M2 receptors function in cholinergic nerve terminals to regulate the release of acetylcholine, whereas M1 receptors are located on postsynaptic cells and facilitate cellular excitation (Mash, Flynn, 1985). Since presynaptic cholinergic neurons degenerate in AD while postsynaptic M1 muscarinic receptors remain in tact, the use of long-acting muscarinic agonists like RS-86 has been proposed as a treatment strategy for memory loss. However, RS86 has low brain penetration; combining it with inositol using a linkage which can be metabolized once in the brain may increase bioavailability of the agonist as well as maintaining the beneficial effect of inositol. In the past, both inositol, in the form of 1-fluoro-scyllo-inositol, and RS-86 derivatives have been radiolabeled with F-18 or C-11 as potential PET probes for AD.

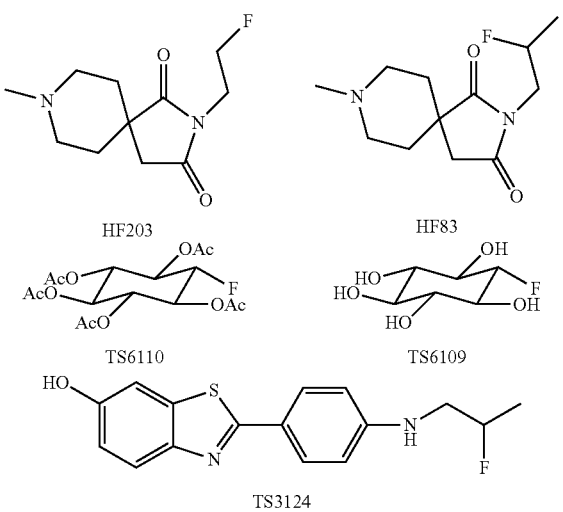

-continued

HF621

HF87

8. It is believed that these suitable compounds target mast cells by inhibiting cytokine production therefore an additional treatment the inflammatory response associated with the AD trigger and process. In their previous publication (Jin, Silverman, et al. 2009), Jin and co-workers indicate that the potential cromolyn compounds can be used as a Mast cell inhibitors.

Example 6

Non-Steroidal Anti-Inflammatory Drugs (NSAIDs)

Compelling evidence from multiple epidemiology studies revealed that long-term dosing with non-steroidal anti-inflammatory drugs (NSAIDs) dramatically reduced AD risk in the elderly, including delayed disease onset, reduced symptomatic severity and slowed cognitive decline (Veld, 2001; Etminan, 2003; Imbimbo, 2010). Three mechanisms have been proposed how NSAIDs inhibit the processes that contribute to AD progression: i) by inhibiting COX activity to reduce or prevent microglial activation and cytokine production in the brain (Mackenzie, 1998; Alafuzoff, 2000; Yan, 2003; Gasparini, 2004; Imbimbo, 2010); ii) by reducing amyloid deposition (Weggen, 2001; Yan, 2003; Imbimbo, 2010); or iii) by blocking COX-mediated prostaglandin E2 responses in synapses (Kotilinek, 2008).

Therefore, NSAIDs are predicted to dampen the neuroinflammatory response and impact AD progression via several mechanisms. When administered together with drugs that inhibit beta-amyloidoligomerization, the combination treatment paradigm is proposed to attenuate the multiple triggers leading to neurodegeneration and neuronal death. The decline in cognitive performance may be reversed, due to neuronal plasticity and neurogenesis in the hippocampus (Kohman, 2013), if AD progression is arrested at a very early stage.

Ibuprofen.

Ibuprofen is a non-selective COX inhibitor for treating inflammation as a non-steroidal anti-inflammatory drug (NSAID). The COX enzymes convert certain fatty acids to prostaglandins. The prostaglandins at the end of the "chain" of reactions that starts with the COX enzyme cause an increased sensitivity to pain, fever, and vasodilation (increased blood flow or inflammation). By inhibiting the start of this chain of reactions, ibuprofen therefore reduces pain, fever, and inflammation. Because ibuprofen blocks the activity of both COX enzymes, it is considered a non-selective COX inhibitor NSAID.

ALZT-OP1 therapy for the treatment of individuals with amnestic mild cognitive impairment. ALZT-OP1 is a multi-functional drug therapy consisting of cromolyn sodium (ALZT-OP1a) administered by inhalation to inhibit beta-amyloid peptide polymerization and to dampen immune responses, plus a concomitant but separately administered low dose oral ibuprofen tablet (ALZT-OP1b) to inhibit the neuro-inflammatory response in persons with confirmed amnestic mild cognitive impairment (aMCI) due to Alzheimer's disease. Both active pharmaceutical ingredient (API) drugs in this ALZT-OP1 formulation are approved, marketed drugs that have been re-purposed for use to prevent the onset of dementia and Alzheimer's disease progression.

ALZT-OP1a

The investigational product ALZT-OP1a (cromolyn sodium) is a synthetic chromone derivative that has been approved for use by the FDA since the 1970s for the treatment of asthma. For asthma treatment, cromolyn sodium powder was micronized for inhalation to the lungs via dry powder inhaler, i.e., the Spinhaler device. Liquid intranasal and ophthalmic formulations have also been developed for the treatment of rhinitis and conjunctivitis.

The mechanism of action for cromolyn sodium (ALZT-OP1a) is characterized as a mast cell stabilizer, namely to suppress cytokine release from activated lymphocytes together with preventing the release of histamine from mast cells (Netzer, 2012; Keller, 2011). It was administered four times daily as prophylaxis for allergic and exercise-induced asthma, not as a treatment for acute attacks.

We have discovered a new mechanism of action for cromolyn, which, along with its role for suppressing immune responses, enables the re-purposing of this approved drug for use to halt AD progression. Our studies have shown that cromolyn sodium binds to beta-amyloid peptides and inhibits its polymerization into oligomers and higher order aggregates. The inhibition of beta-amyloid polymerization will arrest amyloid-mediated intoxication of neurons and restore the passage of these aberrant beta-amyloid oligomers out of the brain rather than their accumulation.

Our studies showed that cromolyn penetrates the blood-brain barrier in animal models, so that plasma bioavailability following cromolyn inhalation will translate to concentrations in the brain sufficient to interfere with beta-amyloid oligomerization and accumulation. Inhalation of cromolyn sodium was shown to be the most effective non-injected administration route for systemic bioavailability of cromolyn sodium in animals and humans (Moss, 1970; Neale, 1986; Richards, 1987; Aswania, 1999; Tronde, 2003). An FDA-approved route of administration for cromolyn sodium is oral inhalation using a capsule-based dry powder inhaler, with 20 mg cromolyn sodium loaded per capsule. Studies have shown that with high inspiratory rates, the inhaled cromolyn sodium is delivered efficiently to the human lung, with 10-15% of the inhaled drug-delivered-dose absorbed into the bloodstream (Richards, 1987; Keller, 2011). For these reasons, cromolyn sodium inhalation with a dry powder inhaler device was selected as the route of administration in this study. However, plasma levels of cromolyn following inhalation are reported to show high intra- and inter-subject variability, and that cromolyn uptake by asthmatics was lower than in healthy volunteers (Richards, 1987; Keller, 2011).

Cromolyn sodium powder blend (ALZT-OP1a) will be loaded into blisters for use with a dry powder inhaler with reproducible aerosol performance at a range of inspiratory rates. Each blister will contain the active product ingredient (cromolyn sodium) and inhalation grade lactose monohydrate as an excipient. The once-daily cromolyn dose to be tested in this study is less than 20% the dose from the four-times daily approved dose level (80 mg cromolyn sodium total per day) for the treatment of asthma. The dose is calculated to titrate the estimated daily 22-27 nanogram of Aβ amyloid plaque produced in the brain.

Taken together, the once daily ALZT-OP1a dose in this study should preserve the drug's excellent safety and tolerability profile, yet is predicted to achieve the nanomolar drug concentrations needed to block beta-amyloid oligomerization in the brain to prevent Alzheimer's disease progression.

ALZT-OP1b (ibuprofen). The generic name is iso-butyl-propanoic-phenolic acid. ALZT-OP1b is an over the counter drug, taken in orally and does not require prescription. Ibuprofen has a long safety history. The drug is used for pain, fever, sports injuries and gastrointestinal problems. The weight dosage independence has been indicated on the drug package.

The investigational product ALZT-OP1b (ibuprofen) is non-selective COX inhibitor for treating inflammation as a non-steroidal anti-inflammatory drug (NSAID). The COX enzymes convert certain fatty acids to prostaglandins. The prostaglandins at the end of the "chain" of reactions that starts with the COX enzyme cause an increased sensitivity to pain, fever, and vasodilation (increased blood flow or inflammation). By inhibiting the start of this chain of reactions, ibuprofen therefore reduces pain, fever, and inflammation. Because ibuprofen blocks the activity of both COX enzymes, it is considered a non-selective COX inhibitor NSAID.

As described above, dampening the neuro-inflammatory response will impact AD progression by several mechanisms. Ibuprofen, which crosses the human blood brain barrier (Bannworth, 1995; Parepally, 2006), dampens the production of pro-inflammatory cytokines (Gasparini, 2004), which should contribute to its utility for preventing AD progression. However, NSAIDs, such as rofecoxib and naproxen, for the treatment of AD has been inconclusive or contributed to higher risk of AD progression when administered as the sole therapy in clinical trials (Thal, 2005; Imbimbo, 2010) despite the multiple epidemiology studies showing reduced AD risk in individuals taking NSAIDs, including ibuprofen (Veld, 2001; Etminan, 2003). Besides the criticism surrounding the choice of rofecoxib and naproxen as the NSAIDs for sole therapy in AD (Gasparini, 2004), the ADAPT rofecoxib/naproxen treatment trial was conducted with subjects exhibiting mild-to-moderate AD (Aisen 2003; Breitner, 2011). Given the epidemiology data, it has been hypothesized that NSAID administration may be beneficial only very early indisease (Imbimbo, 2010; Breitner, 2011). The aMCI patient population is therefore the group that we have selected to be tested in this clinical study.

It is important to note that in the NSAID epidemiology studies, AD risk decrease was restricted to NSAIDs that presumably lower beta-amyloid (42-)peptide levels, such as ibuprofen and indomethacin (Gasparini, 2004; Imbimbo, 2010), and long-term dosing with low NSAID doses were equally effective as higher doses (Broe, 2000; Breitner 2001). Hence, in one cohort in this AZTherapies ALZT-OP1 trial, oral ibuprofen will be administered as tablets (ALZT-OP1b) at a dose lower (less than 5%) of the lowest over-the-counter approved dose. In combination with cromolyn sodium inhalation treatment (ALZT-OP1a), we will test the hypothesis that dampening the low level neuroinflammatory response with ibuprofen will contribute significantly to preventing cognitive decline due to Alzheimer's disease progression. The dose is calculated to titrate the estimated invisible inflammatory response at the early stages of the disease.

Uncontrolled ibuprofen dosage is associated with several side effects such as nausea, headache, ulcers, dizziness, and hypertension. A minor number of cases can cause heart or renal failures. The overdose of ibuprofen can be dangerous. The proposed daily dose for this clinical trial is 20 fold lower than the dose over the counter, and the total yearly dose totaled from the chronic daily dose is less than a total weekly dose over the counter. It is not expected that the yearly toxicity will exceed the weekly over the counter dose.

Risk Benefits of ALZT-OP1 (Cromolyn)

The main goal for using ALZT-OP1 in aMCI subject is its predicted multifunctional treatment of the early appearance signs of cognitive impairment associated with Alzheimer's Disease. Low dose of ALZT-OP1a is expected to control Aβ oligomerization and slow down the extra cellular Aβ fibril brain accumulation. At the same time, low dose of ALZT-OP1a can inhibit cytokine production from the high brain must cell concentration. The low dose ALZT-OP1b (ibuprofen), a known non-specific COX inhibitor, is expected to control the inflammatory response associated with Aβ plaque formation. The main benefits of the low dose chronic daily use are to control and slow down the earlier AD pathophysiology cascade of the main events that trigger intracellular tau tangles and neuron degeneration. ALZT-OP1 treatment will slow down later AD stages manifestation, prolong the patient's life, better control the quality of life and significantly lower the expensive cost of family and nursing treatment and human resources.

Both medications are approved for treatment since the seventies. Both drugs displayed excellent safety profile at much higher dosages. However, each of the drugs have its own short and chronic treatment side effects for the used dosages.

AZLT-OP1a has a long history of safety in adults and children. Cromolyn sodium is available as metered-dose inhalers, and used for long-term asthma prevention ad control by decreasing inflammation and improving lung function. Cromolyn blocks cytokine release of mast cells that cause airways inflammation. The drug is associated with very mild side effects, like coughing, skin rash, and headaches. The treatment doses in this clinical trial are 4-8 folds lower that prescribed and are not expected to cause any significant higher toxicity that the asthma dose.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

REFERENCES

1. JOURNAL OF PHARMACEUTICAL SCIENCES, VOL. 92, NO. 6, JUNE 2003
2. *J. Pharm. Sci.* 1977, 66, 1-19.
3. *J. Neuroimmunol.* 1984, 7, 27
4. U.S. Pat. No. 7,858,803.
5. U.S. Pat. No. 6,972,127.

6. U.S. Pat. No. 6,946,116.
7. U.S. Pat. No. 6,696,039.
8. U.S. Pat. No. 6,168,776.
9. U.S. Pat. No. 5,594,142.
10. U.S. Pat. No. 4,481,206.
11. U.S. Pat. No. 4,405,735.
12. U.S. Patent Application Publication No. 2011/0060138.
13. Netzer N. C. et al, "The actual role of sodium cromoglycate in the treatment of asthma—a critical review" *Sleep Breath* (2012) 16, 1027-1032.
14. Keller, M. and Shierholz, J. "Have inadequate delivery systems hampered the clinical success of inhaled disodium cromoglycate? Time for reconsideration" (2011) 8, 1-17.
15. Moss, G. F. and Ritchie, J. T., "The Adsorption and Clearance of Disodium Cromoglycate from the Lung in Rat, Rabbit, and Monkey" *Toxicol. Applied Pharmacol.* (1970) 17, 699-707.
16. Neale, M. G. et al, "The pharmacokinetics of sodium cromoglycate in man after intravenous and inhalation administration". *Br. J. Clin. Pharmacol.* (1986) 22: 373-382.
17. Richards, et. al, "Absorption and Disposition Kinetics of Cromolyn Sodium and the Influence of Inhalation Technique". *J. Pharmacol. Exp. Therapeutics* (1987) 241, 1028-1032.
18. Aswania, O. A. et al, "Relatively bioavailability of sodium cromoglycate to the lung following inhalation, using urinary excretions". *J. Clin. Pharmacol.* (1999) 47, 613-618.
19. Tronde, A. et al, "Pulmonary Absorption Rate and Bioavailability of Drugs In Vivo in Rats: Structure-Absorption Relationships and Physicochemical Profiling of Inhaled Drugs" *J. Pharm. Sci.* (2003) 92, 1216-1233.
20. Jin Y, Silverman A J, Vannucci S J. "Mast cells are early responders after hypoxia-ischemia in immature rat brain." *Stroke.* 2009 September; 40 (9):3107-12.
21. Aisen P. S. et al, "Effects of Rofecoxib or Naproxen vs. Placebo on Alzheimer Disease Progression" *JAMA* (2003) 289, 2819-2826.
22. Alafuzoff, I. et al, "Lower counts of Astroglia and Activated Microglia in Patients with Alzheimer's Disease with Regular Use of Non-Steroidal Anti-inflammatory Drugs" *J. Alz. Dis.* (2000) 2, 37-46.
23. Albert K. S. and Gernaat, C. M., "Pharmacokinetics of ibuprofen" *Am. J. Med* (1984a) 13, 40-46.
24. Albert, K. S. et al, "Effects of age on clinical pharmacokinetics of ibuprofen" *Am. J. Med.* (1984b) 13, 47-50.
25. Aswania, O. A. et al, "Relatively bioavailability of sodium cromoglycate to the lung following inhalation, using urinary excretions". *J. Clin. Pharmacol.* (1999) 47, 613-618.
26. Bannworth, B. "Stereoselective disposition of ibuprofen enantiomers in human cerebrospinal fluid" *Br. J. Clin. Pharmacol.* (1995) 40, 266-269.
27. Beach, J. E. et al, "Cromolyn Sodium Toxicity Studies in Primates" *Toxicol. Appl. Pharmacol.* (1981) 57, 367-400.
28. Breitner, J., "Alzheimer's disease: the changing view" *Annals Neurol.* (2001) 49, 418-419.
29. Breitner, J. C. et al, "Extended results of the Alzheimer's disease anti-inflammatory prevention trial" *Alz. Dementia* (2011) 402-411.
30. Broe, G. A. et al, "Anti-inflammatory drugs protect against Alzheimer's disease at low doses". *Arch Neurol.* (2000) 57, 1586-1591.
31. Cummings, J. L., "Alzheimer's Disease". *N Engl J Med* (2004) 351, 56-67.
32. Doody, R. S. et. al., "Donepezil treatment of patients with MCI". *Neurology* (2009) 72, 1555-1581.
33. Davies, N. M. "Clinical Pharmacokinetics of Ibuprofen: the first 30 years" *Clin Pharmacokinetics* (1998) 34, 101-158.
34. Etminan, M. et. al., "Effect of non-steroidal anti-inflammatory drugs on risk of Alzheimer's disease: systematic review and meta-analysis of observational studies". *Brit. Med. Journal* (2003) 327, 1-5
35. Gasparini, L. et al, "Non-steroidal anti-inflammatory drugs (NSAIDs) in Alzheimer's disease: old and new mechanisms of action". *J. Neurochem* (2004) 91, 521-536.
36. Griffin, T. S., "What causes Alzheimer's?" *The Scientist* (2011) 25, 36-40.
37. Gwin, E. et al, "Cromolyn sodium in the treatment of asthma associated with aspirin hypersensitivity and nasal polyps" *Chest* (1977) 72, 148-153.
38. Haass, C. and Selkoe, D. J., "Soluble protein oligomers in neurodegeneration: lessons from the Alzheimer's amyloid β-peptide". *Nature Reviews Mol. Cell Biol.* (2007) 8, 101-112.
39. Hashimoto, T. et al, "Apolipoprotein E, especially Apolipoprotein E4, Increases the Oligomerization of amyloid beta Peptide", *J. Neurosci.* (2012) 32, 15181-15192.
40. Heneka, M. et al, "Acute treatment with the PPARγ agonist pioglitazone and ibuprofen reduces glial inflammation and Aβ 1-42 levels in APPV717I transgenic mice". *Brain* (2005) 128, 1442-1453.
41. Hoozemans, J. J. M., et al, "Soothing the Inflamed Brain: Effect of Non-Steroidal Anti-Inflammatory Drugs on Alzheimer's Disease Pathology". *CNS & Neurological Disorders—Drug Targets* (2011) 10, 57-67.
42. Imbimbo, B. et al, "Are NSAIDs useful to treat Alzheimer's disease or mild cognitive impairment" *Front. Aging Neurosci* (2010) 2 (article 19), 1-14.
43. Karran, E. et al, "The amyloid cascade hypothesis for Alzheimer's disease: an appraisal for the development of therapeutics" *Nature Reviews* (2011) 10, 698-712.
44. Keller, M. and Shierholz, J. "Have inadequate delivery systems hampered the clinical success of inhaled disodium cromoglycate? Time for reconsideration" (2011) 8, 1-17.
45. Knowles, J., "Donepezil in Alzheimer's disease: an evidence-based review of its impact on clinical and economic outcomes". *Core Evidence* (2006) 1, 195-219.
46. Kohman, R. A. and Rhodes, J. S., "Neurogenesis, inflammation and behavior". *Brain, Behavior, and Immunity* (2013) 27: 22-32.
47. Kotilinek, L. et al, "Cyclooxygenase-2 inhibition improves amyloid-β-mediated suppression of memory and synaptic plasticity". *Brain* (2008) 131: 651-664.
48. Krstic, D. and Knuesel, I., "Deciphering the mechanism underlying late-onset Alzheimer disease", *Nature Reviews Neurology*, (2012): 1-10.
49. Mackenzie, I. R. and Munoz, D. G., "Nonsteroidal anti-inflammatory drug use and Alzheimer-type pathology in aging". *Neurology* (1998) 50, 986-990.
50. Neale, M. G. et al, "The pharmacokinetics of sodium cromoglycate in man after intravenous and inhalation administration". *Br. J. Clin. Pharmacol.* (1986) 22: 373-382.
51. Parepally, J. M. R. et al, "Brain Uptake of Nonsteroidal Anti-Inflammatory Drugs: Ibuprofen, Flurbiprofen, and Indomethacin" *Pharm. Research* (2006) 23, 873-881.

52. Pehourcq, F. et al, "Diffusion of arylpropionate nonsteroidal anti-inflammatory drugs into the cerebrospinalfluid: a quantitative structure-activity relationship approach" *Fundamental Clin. Pharmacol.* (2004) 18, 65-70.
53. Petersen, R. C. et al, "Vitamin E and Donepezil for the Treatment of Mild Cognitive Impairment" *N. Engl. J. Med.* (2005) 352, 1-10.
54. Schneider, L. S. and Sano, M., "Current Alzheimer's disease clinical trials: Methods and placebo outcomes" *Alz & Dementia* (2009) 5, 388-397.
55. Thal, L. J. et al, "A Randomized, Double-Blind, Study of Rofecoxib in Patients with Mild Cognitive Impairment" *Neuropsychopharmacology* (2005) 30, 1204-1215.
56. Tronde, A. et al, "Pulmonary Absorption Rate and Bioavailability of Drugs In Vivo in Rats: Structure-Absorption Relationships and Physicochemical Profiling of Inhaled Drugs" *J. Pharm. Sci.* (2003) 92, 1216-1233.
57. Veld, B. et al, "Nonsteroidal Antiinflammatory Drugs and the Risk of Alzheimer's Disease". *N Engl. J. Med* (2001) 345, 1515-1521.
58. Weggen, S. et al, "A subset of NSAIDs lower amyloidogenic Abeta42 independently of cyclooxygenase activity". *Nature* (2001) 414, 212-216.
59. Yan, Q., et al, "Anti-Inflammatory Drug Therapy Alters β-Amyloid Processing and Deposition in an Animal Model of Alzheimer's Disease" *J. Neurosci.* (2003) 23, 7504-7509.
60. Zlokovic, B, "Neurovascular pathways to neurodegeneration in Alzheimer's disease and other disorders". *Nature Reviews Neurosci.* (2011) 12, 723-738.
61. Ono M, Hayashi S, Kimura H, Kawashima H, Nakayama M, Saji H., "Push-pull benzothiazole derivatives as probes for detecting beta-amyloid plaques in Alzheimer's brains". *Bioorg Med Chem.* 2009 Oct. 1; 17(19):7002-7. doi: 10.1016/j.bmc.2009.08.032. Epub 2009 Aug. 20.
62. McLaurin J, Kierstead M E, Brown M E, Hawkes C A, Lambermon M H, et al. *Nat Med.* 2006 July; 12 (7):801-8.
63. Sun Y, Zhang G, Hawkes C A, Shaw J E, McLaurin J, Nitz M. *Bioorg Med Chem.* 2008; 16 (15):7177-7184.
64. Wettstein A, Spiegel R. *Psychopharmacology* 1985, 84:572-3.
65. Mash D C, Flynn D D, Potter L T. *Science,* 1985, 228 (4703): 1115-7.
66. Palacios, J. M., Bolliger, G., Closse, A., Enz, A., Gmelin, G. & Molanowski, J. (1986). "The pharmacological assessment of RS-86 (2-ethyl 8-methyl-2, 8-diazaspiro[4, 5]-decan-1, 3-dion hydrobromide). Apotent, specific muscarinic acetylcholine receptor agonist". Eur. J. Pharmacol., 125, 45-62.

I claim:

1. A method of treating a disease or condition in a subject in need thereof comprising co-administering about 10 mg/day of ibuprofen, and a therapeutically effective amount of a second compound, wherein the disease or condition is Alzheimer's disease, dementia, an amyloidosis-associated condition, or a head injury; the second compound is selected from the group consisting of bapineuzumab, solanezumab, gammaglobulin IV, and PF-4360365; and the ibuprofen and the second compound, taken together, are therapeutically effective.

2. The method of claim 1, wherein the ibuprofen is formulated as a pill, capsule, or liquid.

3. The method of claim 1, wherein the ibuprofen is co-administered orally.

4. A method of slowing the progression of a disease or condition in a subject in need thereof comprising co-administering about 10 mg/day of ibuprofen, and a therapeutically effective amount of a second compound, wherein the disease or condition is Alzheimer's disease, dementia, an amyloidosis-associated condition, or a head injury; the second compound is selected from the group consisting of bapineuzumab, solanezumab, gammaglobulin IV, and PF-4360365, and the ibuprofen and the second compound, taken together, are therapeutically effective.

5. The method of claim 4, wherein the ibuprofen is formulated as a pill, capsule, or liquid.

6. The method of claim 4, wherein the ibuprofen is co-administered orally.

* * * * *